United States Patent [19]

Ambos et al.

[11] Patent Number: 4,680,708
[45] Date of Patent: Jul. 14, 1987

[54] METHOD AND APPARATUS FOR ANALYZING ELECTROCARDIOGRAPHIC SIGNALS

[75] Inventors: Hans D. Ambos; Michael E. Cain; Burton E. Sobel, all of St. Louis, Mo.

[73] Assignee: Washington University, St. Louis, Mo.

[21] Appl. No.: 668,245

[22] Filed: Nov. 5, 1984

Related U.S. Application Data

[63] Continuation-in-part of Ser. No. 591,647, Mar. 20, 1984, abandoned.

[51] Int. Cl.⁴ .............................. A61B 5/04; G06F 15/42
[52] U.S. Cl. .................................. 364/417; 128/703; 128/705; 128/702
[58] Field of Search ............... 364/417, 415, 413, 487, 364/484, 485; 128/703, 705, 702; 307/522, 525, 357; 328/138, 140

[56] References Cited

U.S. PATENT DOCUMENTS

| | | | |
|---|---|---|---|
| 4,094,308 | 6/1978 | Cormier | 364/415 |
| 4,170,992 | 10/1979 | Dilliman | 364/417 X |
| 4,211,237 | 7/1980 | Nagel | 364/417 X |
| 4,289,141 | 9/1981 | Cormier | 128/713 |
| 4,296,755 | 10/1981 | Judell | 128/705 |
| 4,422,459 | 12/1983 | Simson | 128/702 |
| 4,432,375 | 2/1984 | Angel et al. | 128/705 |
| 4,458,691 | 7/1984 | Netravali | 128/705 |
| 4,458,692 | 7/1984 | Simson | 128/705 |
| 4,492,235 | 1/1985 | Sitrick | 128/705 |
| 4,501,279 | 2/1985 | Seo | 128/663 |
| 4,510,944 | 4/1985 | Porges | 128/671 |
| 4,559,602 | 12/1985 | Bates, Jr. | 364/487 |

Primary Examiner—Joseph Ruggiero
Assistant Examiner—Charles B. Meyer
Attorney, Agent, or Firm—Ciotti & Murashige

[57] ABSTRACT

ECG signals are digitized and a template representative of an arrhythmia free interval for a particular patient is formed. Subsequent ECG signals which match the template are averaged to form averaged ECG signals to reduce noise. A fast Fourier transform (FET) is performed on the terminal 40 millisecond portion of the QRS complex and the ST segment. The 60 db area and 40 Hz intercept of the resultant spectral output are used as a figure of merit in predicting the liklihood of a particular patient experiencing ventricular tachycardia. Alternatively, the FET magnitude is squared to form energy spectra of the ECG signals and a measure of the energy in a first preselected portion such as the 20-50 Hz region is compared with a second preselected portion such as the entire spectra to form a figure of merit for predicting ventricular tachycardia.

35 Claims, 35 Drawing Figures

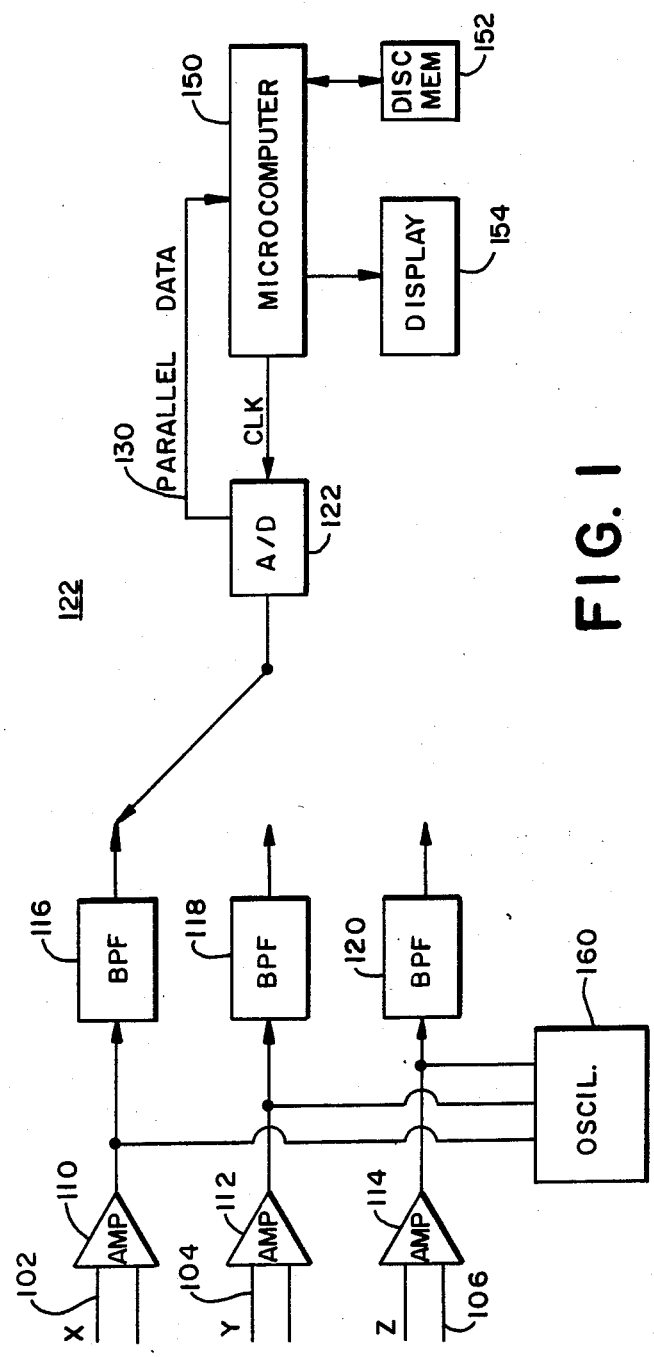

METHOD AND APPARATUS FOR ANALYZING ELECTROCARDIOGRAPHIC SIGNALS

BACKGROUND OF THE INVENTION

This is a continuation-in-part of application Ser. No. 591,647, filed Mar. 20, 1984, now abandoned.

This invention relates to electrocardiography and, more particularly, to a method and apparatus for predicting risk for development of malignant ventricular arrhythmias.

Many patients who have suffered heart damage via a myocardial infarction are in danger of sudden death from acute arrhythmia. The ability to reliably and noninvasely predict the risk for development of such arrhythmias in patients is desirable.

Recently high gain amplification and signal processing techniques in the time domain have detected low amplitude, high frequency potentials in the terminal QRS complex and ST segments of signal averaged electrocardiograms (ECG's) obtained during arrhythmia free intervals from patients and experimental animals with sustained ventricular tachycardia. Recent studies of these patients with time domain analysis have used a variety of low (25 to 100 Hz) and high (250 to 300 Hz) band pass filters. A major limitation of these time domain procedures is the lack of a priori knowledge of the frequency distribution of the signals of interest and hence the inherent risk that filtering will exclude signals of particular interest. Fast Fourier Transform (FET) analysis is a powerful analytic method that is complimentary to time domain analysis and avoids some of the limitations of a priori filtering. Moreover, FET analysis facilitates identification and characterization of frequencies independent of regional amplitude and is thus particularly well suited for assessing low amplitude signals. Finally, this system and FET analysis provide flexibility for analyzing different ECG regions using the same system hardware and software.

As another example of time domain analysis, U.S. Pat. No. 4,442,459 (Simson) discloses applying the latter portions of the X, Y, and Z digital QRS signals in reverse time order to a digital high pass filter to eliminate a ringing artifact from the filter output. The resulting filtered outputs are combined to create a filtered QRS which is examined and the last 40 milliseconds of which is isolated and measured to obtain an indication of the level of high energy content. The initial portion of the QRS wave form is also processed in a forward direction to obtain an indication of the QRS total duration.

SUMMARY OF THE INVENTION

An object of the present invention is to provide a noninvasive electrocardiographic system capable of improved objective identification and characterization of low amplitude potentials in the surface ECG signal.

The X, Y, and Z ECG signals are amplified, recorded over a broad bandwidth, converted from analog to digital, processed to select normal QRS waveforms, and signal averaged to reduce the noise level. A fast Fourier transform is then performed on the terminal 40 milliseconds of the QRS complex and ST segments of each of the averaged X, Y, and Z ECG signals. The resultant spectral outputs are examined and a figure of merit created to obtain a characterization of the frequency content of the various portions of the signal averaged ECG examined.

In one embodiment the magnitude of the FFT is first squared to form energy spectra of the ECG signals. An energy measure of a first preselected portion such as the 20 to 50 Hz region is compared with an energy measure of a second preselected portion such as the entire energy spectra to determine the presence or absence of a predetermined frequency content in a predetermined portion of the ECG signals such as the combined QRS terminal 40 milliseconds and ST region. The comparison includes taking the magnitudes of the peaks in the first preselected portion of a spectrum and comparing them with the magnitude of the largest peak of the spectrum. Also the area under the spectrum curve in the first preselected portion is compared with the area of the 0 to 20 Hz region.

The peak magnitude and area comparisons after further operation are called the magnitude ratio and area ratio. Since a plurality of ECG leads are used with each patient when monitoring the ECG, a mean value formed from all ECG leads for the magnitude ratio and area ratio is formed for each patient.

BRIEF DESCRIPTION OF THE DRAWINGS

FIG. 1 is a block diagram of a preferred embodiment of the present invention.

DETAILED DESCRIPTION OF THE DRAWINGS

Figure 2A:
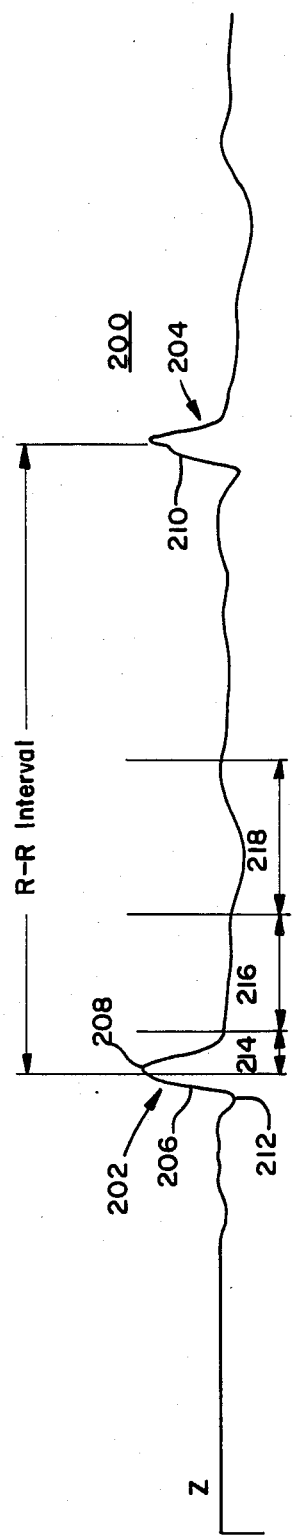
FIG. 2A is a representative signal averaged ECG from one of the leads of FIG. 1 showing various segments of the ECG signal and the R—R interval.

Referring now to FIG. 1, a block diagram of the present invention designated generally 100 is shown including standard bipolar X, Y, and Z electrocardiogram (ECG) leads 102, 104, and 106, respectively. Standard Frank X, Y, and Z leads, Model No. 1507-11A, are applied to a patient in accordance with the Model 1507-11A recommended electrode placement. Each of the X, Y, and Z lead signals are amplified (1,000 fold) by Hewlett-Packard 1057 Amplifiers 110, 112, and 114, respectively. The outputs of the amplifiers are passed through band pass filters 116, 118, and 120, respectively, having a bandwidth of 0.05 Hz to 470 Hz. Then the signals are converted from analog to digital signals by A/D converter 122 at a 1 KHz rate having 12 bits of accuracy and a lowest resolution of 1 microvolt. An ADAC Inc. Model No.16SE-C-3P6A-P A/D converter was used.

The input to the A/D converter 122 is switched sequentially among the outputs of filters 116, 118 and 120 with a 300 microsecond delay in between. The digital X, Y and Z signals from A/D converter 122 are provided in parallel over line 130 to microcomputer 150. A floppy disk memory 152 and a Selanar raster graphics display 154 with raster control are coupled to the microcomputer 150. A DEC VT 103 LSI 11/23 microcomputer with 64K bytes of memory was used. The microcomputer 150 along with disk 152 and display 154 can be mounted on a portable cart for use at the patients bedside. The amplified X, Y, and Z signals are simultaneously displayed on the Hewlett-Packard oscilliscope 160 for continuous real time visual monitoring.

Referring now to FIG. 2A, a representative signal averaged Z ECG lead designated generally 200 is shown. Two QRS complexes designated generally 202 and 204 are shown. The large signal 206 is known as the R wave, and its peak 208 is called the fiducial point. The time separation between adjacent R waves 206 and 210 is called the R—R interval. The peak to peak amplitude of the QRS signal is the voltage measured from the positive peak of the R wave at 208 to the negative peak of the QRS waveform at 212.

Each ECG signal can be thought of as including: a terminal QRS signal 214 which comprises the last 40 msec of the QRS complex (end of QRS complex and preceding 40 msec); and an ST segment 216 which extends from the end of the QRS segment 214 to the beginning of the T segment 218 of the ECG signal 200.

Figure 3:
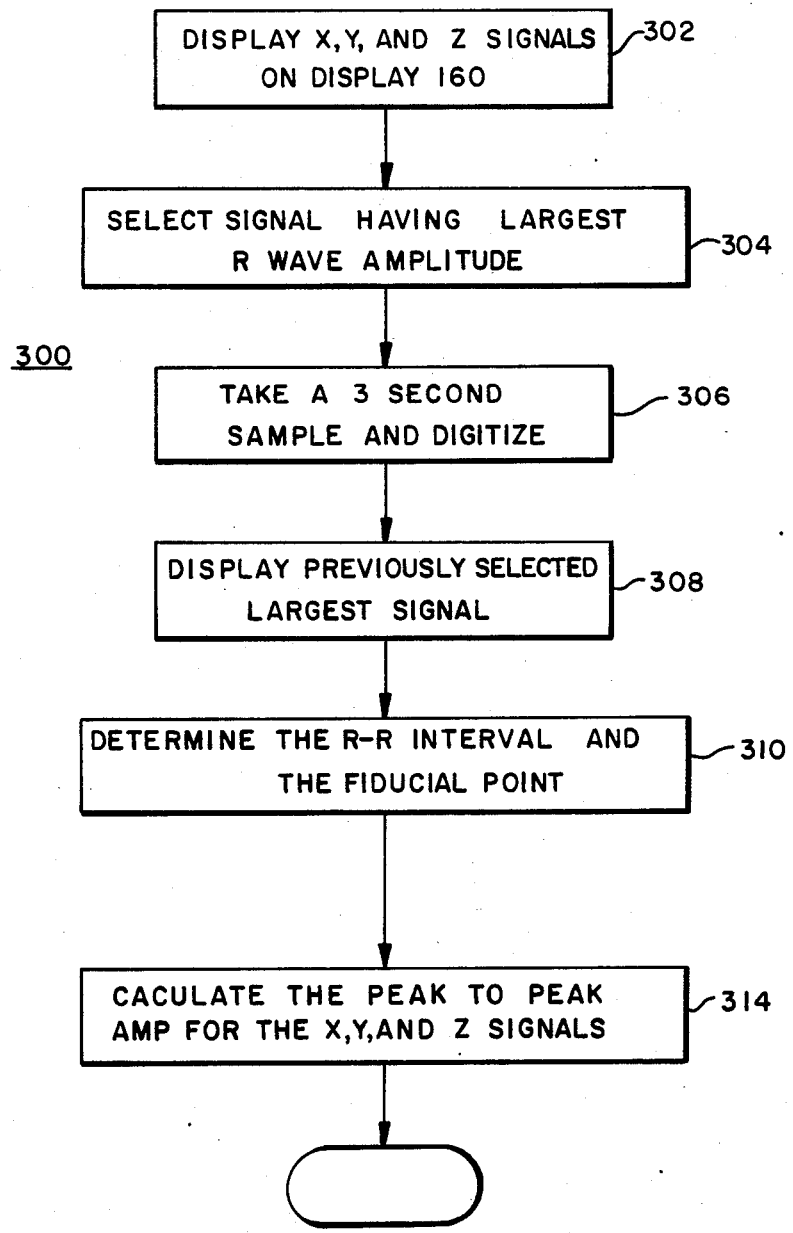
FIG. 3 is a flow chart of the method used for template formation.

Referring now to FIG. 3, a simplified block diagram for template formation designated generally 300 is shown for selecting certain ones of the digital X, Y, and Z signals which are to be considered as arrhythmia-free signals and which are to be used in forming the signal averaged X, Y, and Z ECG signals for further processing. By visual inspection of the display 160, a set of X, Y, and Z signals is chosen which can be considered to represent a display of normal sinus rhythm 302. The signal such as the one having the largest R wave amplitude relative to the P and T points of the ECG signal is selected 304. Then a three second sample of the X, Y and Z leads are digitized and stored 306. The preselected signal 304 is displayed on display 154. See 308. The R—R interval (the distance between adjacent R waves of adjacent QRS complexes) and the fiducial point (peak point 208 of the R wave) are identified using the adjustable cursor accompanying the Selanar display 310. At the same time the QRS amplitudes (peak to peak voltages) for each of the X, Y, and Z signals are determined 314. The R—R interval, fiducial point 208, the X, Y, and Z QRS amplitudes and 40 points of the R waves (20 points on either side of the fiducial point) are then stored at a template in the mini-computer 150 memory. This is done automatically using the DEC graphics software package in combination with the use of the cursors on display 154.

Figure 4:
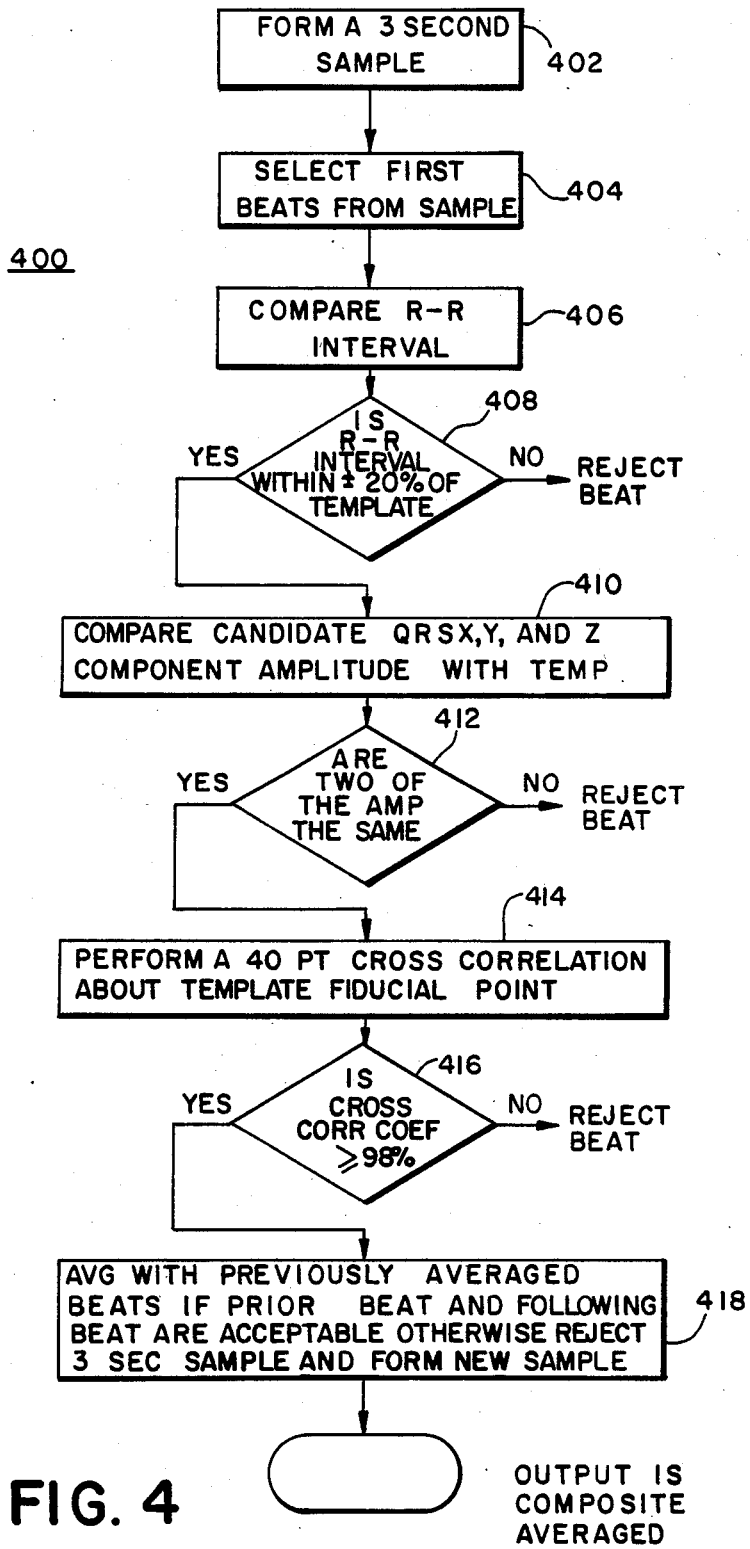
FIG. 4 is a simplified flow chart of the program for selecting and averaging ECG signals.

Referring now to FIG. 4 a process designated generally 400 for selecting arrhythmia free X, Y and Z signals and for averaging ECG signals is shown. Once again, a three second sample of the heartbeat is chosen, digitized, and the digitized X, Y, and Z signals for the three second interval are stored in a circular memory buffer. See 402. The middle beat of these stored three second samples is chosen 404 and the selected signal compared with the template. Specifically, the R—R interval is compared with the template R—R interval 406. If the R—R interval is not within ±20% of the template value the beat is rejected. See 408. Otherwise, the peak to peak amplitudes of the X, Y, and Z signals of the chosen beat are compared with the QRS amplitudes of the template 410. If at least 2 of the 3 amplitudes are the same as the template amplitudes then the beat is selected as a candidate for averaging, otherwise the beat is rejected 412. Then a 40 point cross correlation 414 of the R wave is made with the template waveform about the fiducial point 208. The 40 points which are chosen are 20 points lying on either side of the fiducial point. If the correlation coefficient is not greater than 98% the beat is rejected 416. If the beat passes the amplitude and cross correlation comparisons, then for the current beat to be acceptable, the beat which went before it and the beat which follows it must all be found to be acceptable when compared with the R—R template. If the center beat is found to be unacceptable then it is shifted left in the circular buffer and compared to the next beat. This process goes on in real time and only if buffer overflow occurs do you go back to 404. The X, Y, and Z ECG signals of each acceptable beat are averaged, point by point, with the X, Y, and Z ECG signals of all other acceptable beats until a 100 beat average is created 418.

The above description of the operation of FIG. 4 is done automatically using the FORTRAN program No. 1 (pages 20-25).

Figure 5:
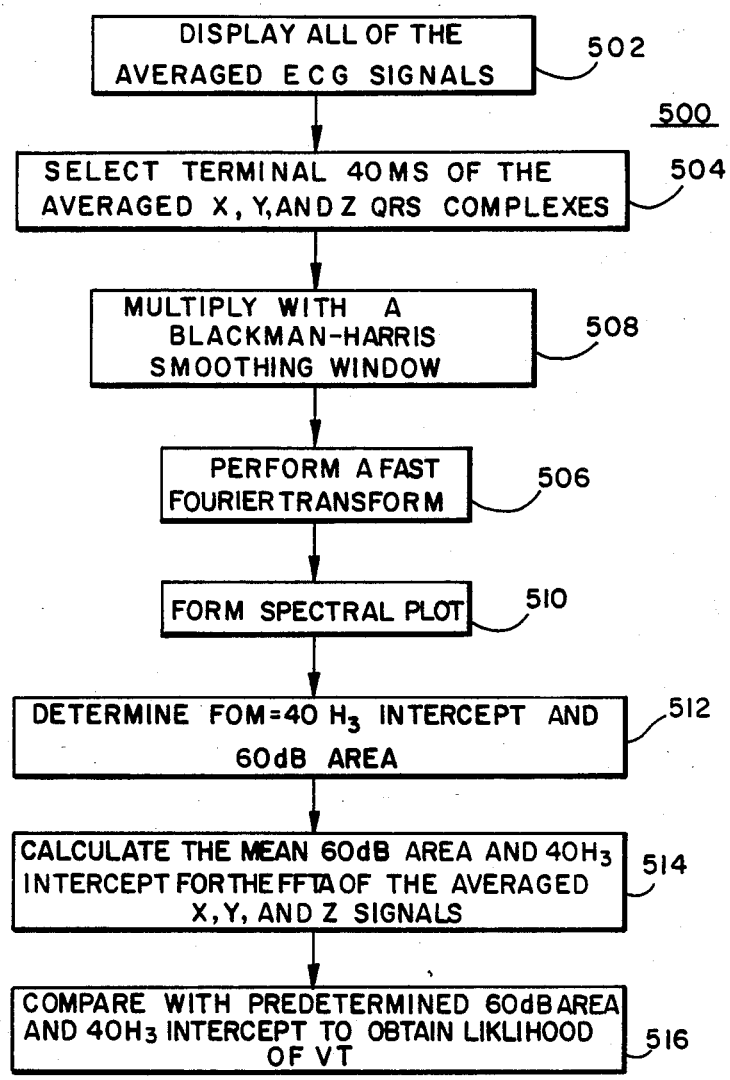
FIG. 5 is a flow chart of the program used for characterizing the frequency content of the averaged ECG signals generated by FIG. 4.
Figures 6A, 6B, 6C, 6D, 6E, 6F:
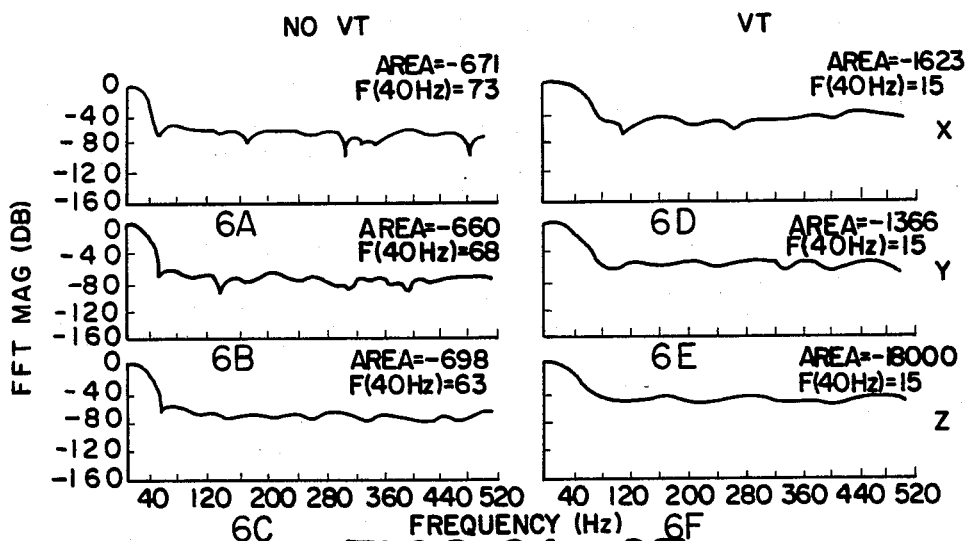
FIGS. 6A through 6F represent the outputs of the program of FIG. 5 operating on a first segment of averaged X, Y and Z ECG signals from a patient with prior myocardial infarction without sustained ventricular tachycardia (VT) and a patient with prior myocardial infarction with sustained VT.
Figures 7A, 7B, 7C, 7D, 7E, 7F:
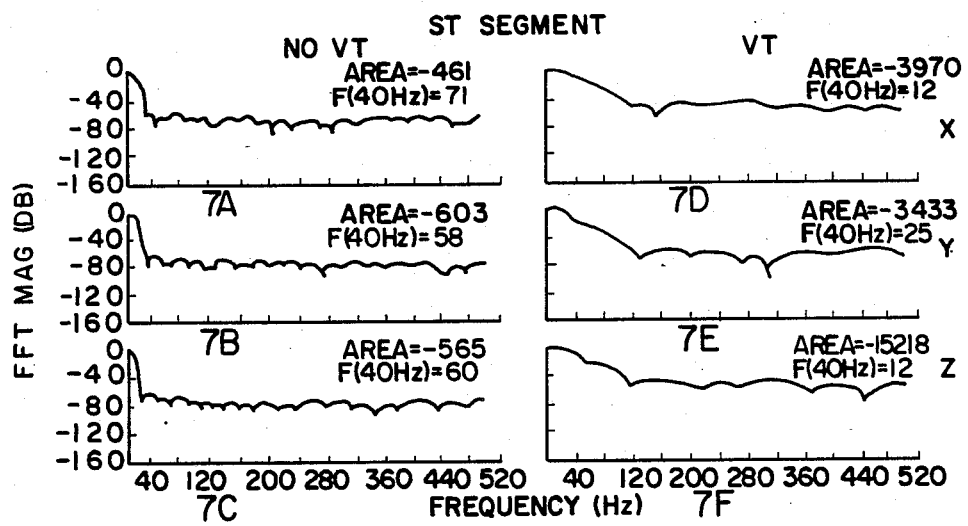
FIGS. 7A through 7F represent the outputs of the program of FIG. 5 operating on a second segment of averaged X, Y and Z ECG signals from a patient with prior myocardial infarction without sustained ventricular tachycardia (VT) and a patient with prior myocardial infarction with sustained VT.

Referring now to FIG. 5, a fast Fourier transform (FFT) analysis 500 is performed on the terminal 40 milliseconds of the QRS complex for each of the averaged X, Y, and Z signals. All of the averaged X, Y and Z QRS signals are stored in memory 152, e.g., the averaged X, Y and Z signals are displayed on display 154. See 502. Using the display cursors, the terminal 40 milliseconds of the QRS signal is determined 504 by finding the end of the QRS complex and sliding 40 msec into the R wave.

A fast Fourier transform (FFT) 506 is performed on the chosen segment of the ECG signal, for example, on the terminal 40 milliseconds of the QRS complex as defined above. The FFT can be performed using any one of a plurality of acceptable commercially available computer programs suitable for use on the particular minicomputer 150, for example, a FORTRAN program from the standard IEEE Library is acceptable and is hereto employed. For the particular segment of the ECG signal chosen a 512 point fast Fourier transform was calculated. The selected sample values (those selected automatically by the cursor) were placed at the beginning of the 512 input array of the FFT program and the remaining values set to zero. This step permitted maintenance of the same frequency scale in the output data but allowed an arbitrary member of input values up to 512.

Fourier analysis assumes that the signal contained in the sample window interval is a repetitive function. If the initial sample point and final sample point are not isopotential, a sharp discontinuity will be introduced between the end of one cycle and the beginning of the next that will artifactually add both high and low frequencies to the original signal. To eliminate this source of error when performing the FFT on discrete components of the ECG (i.e. the terminal 40 msec of the QRS complex) the segment of intersect is multiplied by a four term Blackman-Harris window function 508 to smooth the data to zero at the boundaries 504. See "On the use of windows for harmonic analysis with the discreet Fourier transform", Harris, F. J., PROC IEEE 66:51, 1978 and the FORTRAN program #2 (pages 26-30). The particular Blackman-Harris function used herein had a 6 dB bandwidth, a 92 dB sidelobe level, and a sidelobe falloff of 6 dB per octave. Multiplication of the Blackman-Harris window must be performed before the FFT is calculated.

Figure 2B:
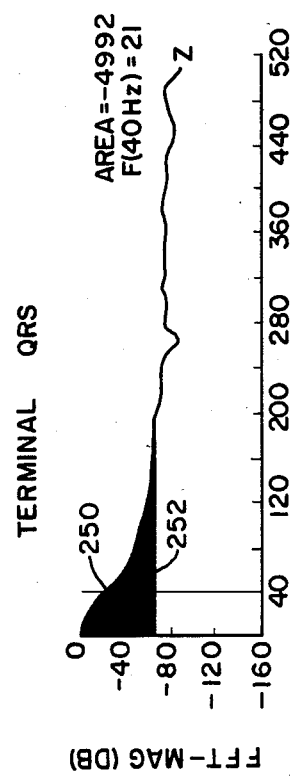
FIG. 2B is a spectral plot of the FFT of the terminal QRS segment of FIG. 2A.

The FFT data are plotted with a high resolution plotter (Versatec, Inc.) 510 and transferred to disk 152 for storage. Referring to FIG. 2B, for each plot, the dB drop at 40 Hz 250 is found and the area 252 under the curve from the fundamental frequency to the frequency at which the amplitude of the spectrum plot drops to 60 dB below the peak level (60 dB area) is determined. (See the FORTRAN program No. 3, pages 31-34.) These two values together form a figure of merit (FOM) 512, FIG. 5, for the spectral plot. The 40 Hz intercept was chosen because most of the energy of a normal QRS is less than 35 Hz and because work by others has shown that fragmented signals have a peak frequency in the 25 to 50 Hz range.

The above mentioned steps of FIG. 5 are performed simultaneously on the averaged X, Y and Z signals and three spectral plots are formed. The mean of the 40 Hz intercept and the 60 dB areas of the FOM's for the averaged X, Y and Z signals is calculated for each patient to generate a single 40 Hz intercept and 60 dB area FOM. The process described in connection with FIG. 5 given above was also performed for ST segment 216 of the averaged X, Y and Z ECG signals. It should be remembered that the ST segment 216 is defined as beginning at the end of the QRS complex and proceeding to the beginning of the T wave. The ST segment is defined using the cursor of the Selanar display.

Using the above-mentioned method, 61 patients were grouped according to clinical characteristics. None was currently receiving antiarrhythmic medications. Group I comprised 16 patients with prior myocardial infarction with at least one documented episode of sustained VT or cardiac arrest that was not associated with a new infarct. Each of the 13 of these 16 patients who was studied in the Clinical Electrophysiology Laboratory at Washington University had inducible sustained VT or VF similar to that occurring clinically. Group II consisted of 35 patients with prior myocardial infarction without a history or documented episode of sustained VT (>30 seconds in duration), syncope, or cardiac arrest who were admitted to the Barnes Hospital Telemetry Unit. All patients in this group were monitored for at least 7 days. Seventeen exhibited absent or simple ventricular ectopy (Modified Lown Class 0 to 1); 18 patients had complex ventricular ectopy (Class 2 to 5), of which nine patients had nonsustained VT. Group III included 10 healthy male controls 24 to 40 years of age with no clinical evidence of organic heart disease or arrhythmias.

There were no significant differences between Groups I and II with regard to age, infarct location, presence of left ventricular aneurysms, or QRS duration. Left ventricular ejection fraction was significantly less in patients with infarction who had manifested sustained VT or VF compared with ejection fraction in Group II patients ($34\% \pm 16$ vs. $45\% \pm 15$, $p<0.02$).

The FFT analysis of FIG. 5 of signal averaged X, Y, and Z ECG signals showed significant differences in the mean 60 dB area and the mean 40 Hz intercept of the terminal 40 msec of the QRS and of the ST segment in patients with prior myocardial infarction and a subsequent episode of sustained VT or VF compared with values in patients with prior myocardial infarction without these arrhythmias and with values in normal subjects. There were no significant differences in the 60 dB area or 40 Hz intercept of the terminal QRS or ST segment in patients with myocardial infarction without sustained VT compared with normal subjects.

Representative plots of FFT analysis of the terminal QRS complex from a patient with prior myocardial infarction without sustained VT and from a patient with prior myocardial infarction with sustained VT are shown in FIGS. 6A-C and 6D-F, respectively. Each depicts power vs frequency plots of the terminal 40 msec of signal averaged QRS complexes recorded from bipolar X, Y, and Z leads along with values for the 60 dB area and the dB drop at the 40 Hz intercept. In each lead, the terminal 40 msec of the QRS complex from the patient who had manifest sustained VT contained relatively more high frequency components than the complex from the patient who had not, reflected by a greater value for the 60 dB area and a lesser dB drop at the 40 Hz intercept. Similar plots were obtained for the FET analysis of the ST segments from the same two patients. In each lead, the ST segment in the signal from the patient who had manifest an episode of sustained VT contained relatively more high frequency components than the ST segment from the patient without VT. Spectral differences in the terminal QRS and ST segment were consistently most marked at frequencies less than 120 Hz.

Based on results of the FFT analysis of FIG. 5 of the terminal 40 msec of the QRS complex in normal subjects (Group III), mean 60 dB area values greater than 2400 and mean 40 Hz intercept values less than 47 dB were defined as abnormal and indicative of an increase in high frequency components in the terminal QRS. Abnormal values for both the 60 dB area and 40 Hz intercept were found in 88% of patients with prior myocardial infarction having a subsequent episode of sustained VT (Group I) and 15% of patients with prior myocardial infarction without sustained VT (Group II).

Based on results of the FFT analysis of FIG. 5 of the ST segment in Group III controls, mean 60 dB values greater than 2500 and mean 40 Hz intercept values less than 52 dB were defined as abnormal and indicative of increased high frequency components in the ST segment. Abnormal values for the 60 dB area of the ST segment were found in 81% and 25% of Group I and Group II patients, respectively. Abnormal values for the 40 Hz intercept were found in 76% and 20% respectively.

Values for both the 60 dB area and 40 Hz intercept of the terminal QRS and ST segment were independent of QRS duration, left ventricular ejection fraction, and complexity of spontaneous ventricular ecopty.

An alternate embodiment of the above invention is now described in connection with FIGS. 8–14. The combined terminal 40 millisecond QRS and ST segment of each signal averaged X, Y and Z lead is identified with the use of the display cursor and standard electrocardiograph criteria 802 and 804. See also FIG. 9 which depicts within cursor lines the combined terminal QRS and ST segment of interest. In a manner similar to FIG. 5, the above region of interest is multiplied by a four-term Blackman-Harris window 806. Next, each of the signal averaged signals is scaled by identifying the maximum magnitude of the averaged signal and setting it to unity 808. Then a 512 point fast-Fourier transform is calculated 810 in a manner as described before in connection with FIG. 5 only now the FFT is performed on the combined terminal 40 millisecond QRS and ST segment. The magnitude of the Fourier transform is then squared 821 to obtain the energy spectrum of the signal and the result is plotted 814.

Figure 10:
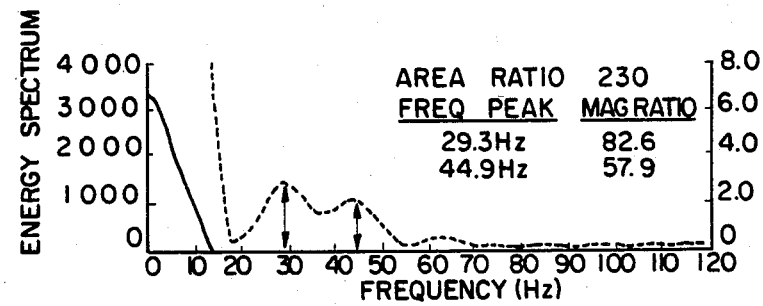
FIG. 10 is a sample energy spectra plot of the signal of FIG. 9 showing the main peak as a solid line on a first scale as marked on the left side and the secondary peaks as a dashd line on a second scale on the right side.
Figures 11A, 11B, 11C, 11D, 11E, 11F:
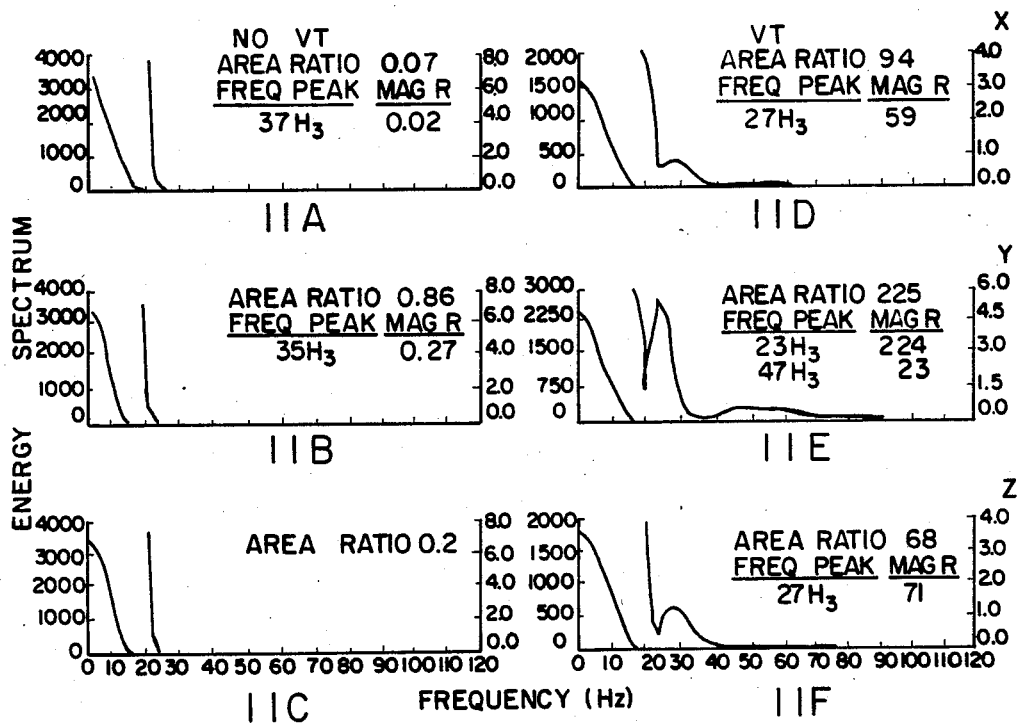
FIGS. 11A through 11F represent the outputs of the program of FIG. 8 operating on a first segment of averaged X, Y and Z ECG signals from a patient with prior myocardial infarction without sustained ventricular tachycardia (VT) and a patient with prior myocardial infarction with sustained VT.
Figures 12A, 12B, 12C, 12D, 12E, 12F:
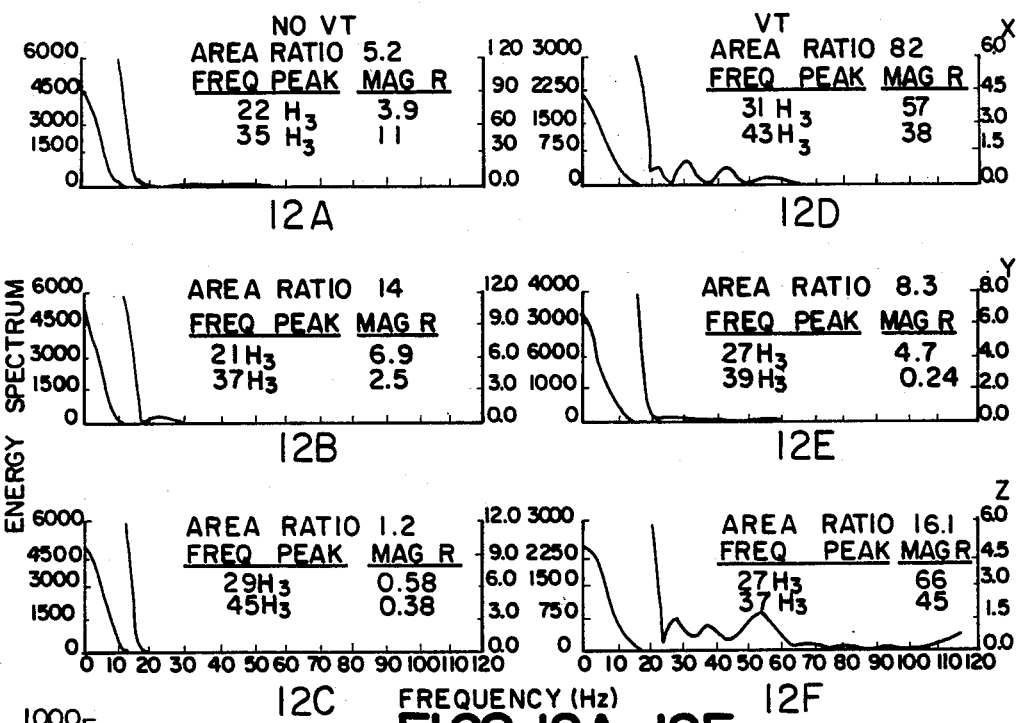
FIGS. 12A through 12F represent the outputs of the program of FIG. 8 operating on a segment of averaged X, Y and Z ECG signals from a patient with prior myocardial infarction without sustained ventricular tachycardia (VT) and a different patient from the patient of FIGS. 11A through 11F with prior myocardial infarction with sustained VT.

A representative plot of an energy spectrum is shown in FIG. 10. To detect smaller peaks which might be obscured by the dominant amplitudes of low frequency components, a second plot (the broken curve in FIG. 10) was generated by dividing the amplitude scale by 500 (see 816). Data was again plotted 818 but data exceeding values in the reduced scale were not plotted. The data was plotted on a high resolution plotter (Versatec, Inc.) and transferred to disc storage.

For each of the spectral plots generated (one for each signal averaged X, Y and Z signal for each patient) the data is first analyzed to locate peaks between 20 and 50 Hz 820. Peaks for the digital data could be defined in several different ways but in the preferred embodiment, a peak is an increase in magnitude for at least two adjacent data points followed by a decrease in magnitude for at least one point. The frequency range of 20 to 50 Hz was chosen after analysis over the bandwidth had demonstrated that frequencies above 70 Hz did not contribute substantially to the terminal QRS and ST segments in any group. Because of potential 60 Hz interference, frequencies between 50 to 70 Hz are not analyzed.

The magnitude of each peak frequency measured on the reduced scale (spectral plot of 818) is divided by the maximum magnitude of the entire signal measured on the initial scale (spectral plot 814) and then multiplied by $10^5$ to form the magnitude ratio 822. The area under the magnified curve (spectral plot 818) between 20 to 50 Hz is divided by the area under the initial curve (spectral plot 814) from 0 to 20 Hz and then multiplied by $10^5$ to form the area ratio 822. The area ratio is computed to determine the relative contribution of components at frequencies between 20 and 50 Hz to frequencies between 0 and 20 Hz.

Figure 8:
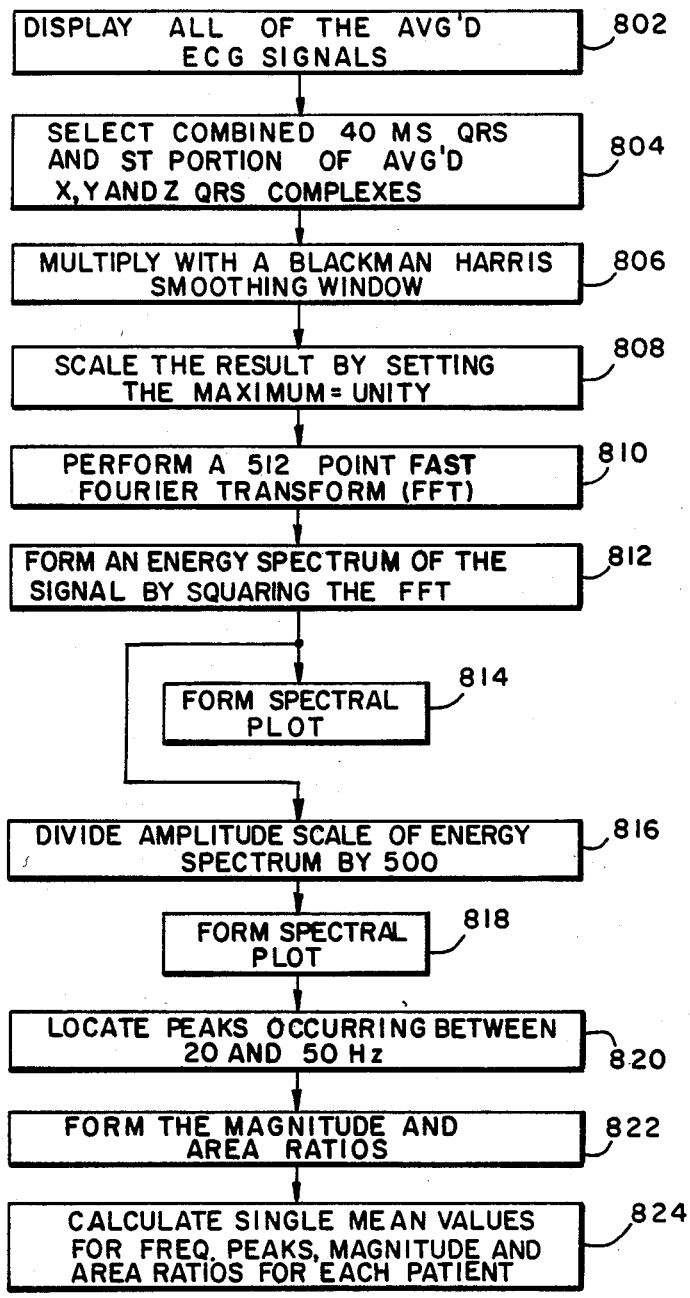
FIG. 8 is a flow chart of an alternate program to that of FIG. 5 used for characterizing the frequency content of the averaged ECG signals generated by FIG. 4.
Figure 9:
FIG. 9 is a representative signal averaged ECG from one of the leads of FIG. 1 showing the combined terminal QRS and ST segment of the ECG signal.

For patient-to-patient comparisons, the X, Y and Z values for peak frequencies are averaged together and expressed as a single number, the mean of X, Y and Z values. The X, Y and Z values for the pre-multiplied magnitude and area ratios are averaged after log transformation and the mean value for both the magnitude and area ratios expressed as antilogs are then multiplied by a constant ($1 \times 10^5$) to facilitate graphic display 824. Program No. 4 implementing the above description of FIG. 8 is provided on pages 35–40.

Using the above described analysis of the energy spectra of the signal averaged X, Y and Z signals, three Groups of patients were studied.

Group I comprised 23 patients, each of whom had sustained prior myocardial infarction and at least one documented episode of sustained ventricular tachycardia or cardiac arrest that was not associated with a new infarct. Group II consisted of 53 patients, each of whom had sustained prior myocardial infarction without sustained ventricular tachycardia (>30 seconds in duration or associated with immediate hemodynamic decompensation), syncope, or cardia arrest. Group III comprised 11 normal subjects.

There were no significant differences in pertinent clinical features between Group I and II with respect to age, locus of infarct, or the presence or absence of left ventricular aneurysm. QRS duration was significantly greater in patients in Group I compared with values in those in Group II ($106 \pm 23$ msec vs $90 \pm 15$ msec; $p<0.01$). Left ventricular ejection fraction was significantly less in patients in group I compared with those in Group II ($35 \pm 14\%$ vs $45 \pm 15\%$; $p<0.01$).

The above analysis of energy spectra of signal averaged X, Y, and Z electrocardiographic recordings showed significant differences in the area ratios and magnitude ratios of peak frequencies of the combined terminal 40 msec of the QRS and ST segments in patients with prior infarction associated with subsequent sustained ventricular tachycardia (Group I) compared with values in patients without sustained ventricular tachycardia (Groups II and III). There were no significant differences in the area ratios in recordings from patients with myocardial infarction without sustained ventricular tachycardia compared with values in normal subjects.

Representative plots of the type described above of squared fast-Fourier transformed data of the terminal QRS and ST segments from a patient with prior myocardial infarction without sustained ventricular tachycardia and from a patient with prior myocardial infarction with sustained ventricular tachycardia are shown in FIGS. 11A–11C and 11D–11F, respectively. Each panel depicts magnitude vs. frequency plots of the combined terminal 40 msec of the QRS complex and ST segments of signal averaged electrocardiographic complexes recorded from bipolar X, Y, and Z leads along with values from the area ratios, peak frequencies, and magnitude ratios. In each lead, the terminal QRS and ST segment from the patient who had manifest sustained ventricular tachycardia contained relatively more high frequency components than the complex from the patient without sustained ventricular tachycardia. The differences in frequency content were more marked between 20 to 50 Hz. The terminal QRS and ST segments from the patient who had no manifested sustained ventricular tachycardia did contain components with frequencies above 20 Hz. However, the overall contribution of these components to the entire signal was modest as reflected by the low area and magnitude ratio values.

FIGS. 12A-12C and 12D-12F illustrates another example of energy spectra of the terminal QRS and ST segments from patients without and with sustained ventricular tachycardia, respectively. The terminal QRS and ST segments from both patients contained components with frequencies between 20 to 50 Hz but differed markedly with respect to the relative contributions of these components to the entire signal. In the X and Z leads, the terminal QRS and ST segments from the patient who had manifest sustained ventricular tachycardia contained a 10 to 100-fold greater proportion of components in the 20 to 50 Hz range compared with corresponding electrocardiographic segments from the patient without sustained ventricular tachycardia.

Figure 13:
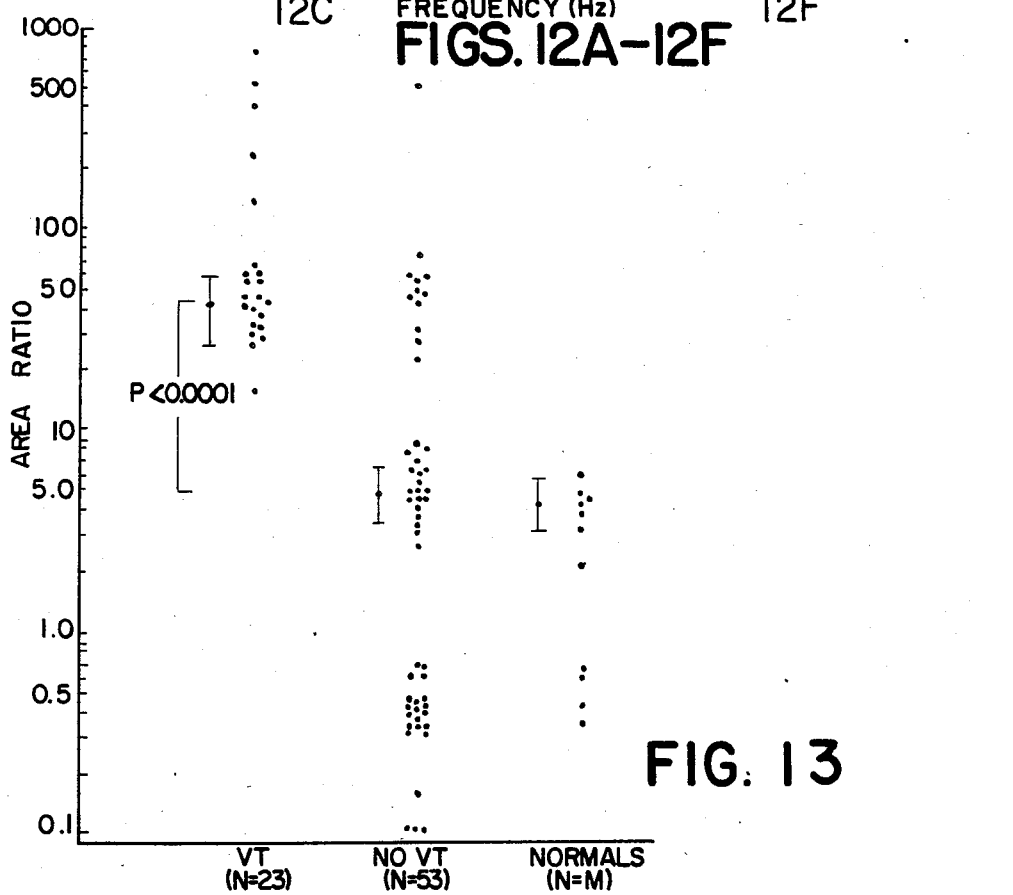
FIG. 13 is a graph comparing the mean area ratios of patients from Groups I, II and III.

Comparisons between values for the area ratios for the three patient groups are shown in FIG. 13. There were significant group differences in area ratio values between patients with prior myocardial infarction who had manifest sustained ventricular tachycardia compared with patients with prior myocardial infarction without sustained ventricular tachycardia and with normal subjects. A 10-fold difference was evident for patients with compared to those without sustained ventricular tachycardia. There was no overlap between values among patients who had manifest sustained ventricular tachycardia and values from normal subjects. However, twelve patients with prior myocardial infarction without clinically documented sustained ventricular tachycardia had area ratios overlapping values from patients who had manifest sustained ventricular tachycardia. It is not yet clear whether these 12 patients are at increased risk for development of sustained ventricular tachycardia.

Figure 14:
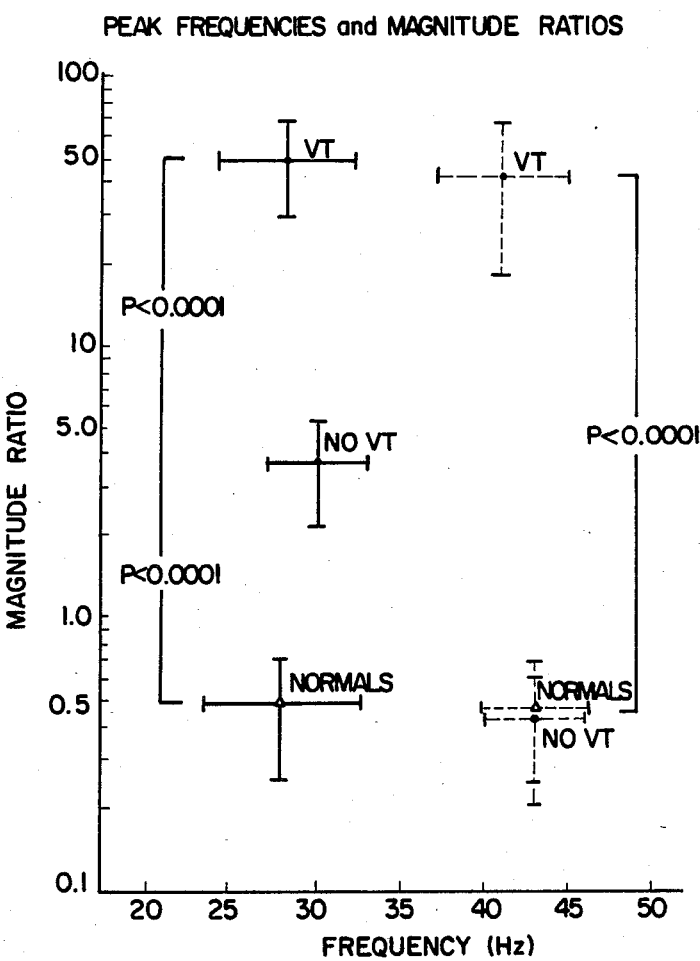
FIG. 14 is a graph comparing the mean magnitude ratios vs. frequency for patients from the Groups I, II, and III.

FIG. 14 illustrates the mean peak frequencies detected between 20 to 50 Hz and the corresponding magnitude ratios for the three patient groups. There were no significant differences in the peak frequencies among patients in the three groups ($28\pm4$ Hz and $41\pm4$ Hz, in Group I; $30\pm3$ Hz and $43\pm3$ Hz, Group II; and $28\pm5$ Hz and $43\pm3$ Hz, Group III). However, the relative contribution of the magnitudes of these peak frequencies to the overall magnitude of the spectral plot of their terminal QRS and ST segments differed significantly. Thus, the terminal QRS and ST segments in patients with prior myocardial infarction who had manifest sustained ventricular tachycardia contained a 10 to 100-fold greater contribution from components in the 20 to 50 Hz range compared with corresponding electrocardiographic segments in patients without sustained ventricular tachycardia. No frequencies above 50 Hz contributed substantially to those electrocardiographic segments in any group.

PROGRAM NO. 1

```
ECG Signal averaging package:

ECGAVG takes an incoming digitized Electrocardiograph signal
and averages normal QRS complexes. ECGAVG has two sections, a learning
period and an averaging period.
    During the learning period, the clinician may choose one of the
three ECG channels X,Y,or Z (channels 0,1,or 2 respectively) for analysis.
The waveform of the desired channel is then displayed at the terminal for
the clinician to mark the peaks of two adjacent normal QRS's. This serves
to set the peak detector threshold, the R-R interval threshold, and to
provide a template waveform for the signal-averaging routines.
    During the averaging period, the clinician enters the number of beats
to average. Once this is done, the peak detector FINDPK looks for signal
values above (or below) the QRS threshold for positive-going (or negative)
QRS's that are within the given R-R interval of each other. If a peak
is found, it is then correlated against the template waveform using ECGCOR.
If the correlation coefficient of the detected peak and the template is
above correlation threshold (right now at about 96% confidence) then the
beat is flagged as a normal QRS. If two such beats are found within the
R-R interval of each other, the second of these two is then averaged into
an array. When the desired number of beats have been averaged, the program
then dumps the three channel names (0,1, and 2) in the order that they have
been averaged (integer values) and then waveform arrays in that same order,
all in unformatted form.

Files for the Signal Averager are:

ECGAVG - Signal averager

ECGPK  - contains subroutine FINDPK, the peak detector.

ECGCOR - contains subroutines 122COR and 124COR for
                       calculating the correlation coefficient over a
                       32 sample point window between an 1*2 an an 1*2
                       array or between an 1*2 and an 1*4 array.
```

ECGFOR — contains the Selenar Graphic driver routines.

ECGMAC — contains the macro routines called by ECGAVG and ECGFOR.

XXLIB — contains the ADAC A/D subroutines.

Once the ECG signal has been averaged, the waveforms may then be displayed on the terminal for windowing using ECGFFT. The unformatted data output files of ECGAVG are read into ECGFFT and displayed at the terminal. The clinician is then asked how many plot sets (windowed sections) are required for the displayed waveform. The clinician then sets the crosshair cursor at the beginning and ending points of each beat section. The data between the cursors is then multiplied by the window funtion (~~a furth order Hamming or something like that~~) and is written out to disk in e13.6 format, preceeded by the number of plot sets (i6 format) and the number of data points (also i6 format). The next set of data points is then windowed and written to disk also preceeded by its number of data points, until the number of plot sets has been reached. The windowed data can then be sent to the Perkin-Elmer for FFTing and plotting.

Files related to ECGFFT are:

ECGFFT — Displays channels X,Y,Z and composite waveforms always in that order and allows sections of the waveforms to be windowed and output to disk in formatted form.

ECGFOR — contains subroutines for Selenar Graphics board.

FFTMAC — contains macro routines called by ECGFFT and ECGFOR.

WINDOW — contains WNDW, the windowing function.

Also FFTNOW does the same thing as ECGFFT but does not window the

Subroutine findpk steps through NPTS sample points at DELD intervals starting at the sample point ISMP and looks for a change in first derivative from pos. to neg. or neg. to pos. If no such point is found (ie: a section of rising or falling or zero slopes) then a 0 is returned.

```
    subroutine findpk(ismp,irtsmp,npts,deld,istat)
    integer snm(9216),smp,ismp,irtsmp,npts,deld,isvmax,i,j,k,
   .        ibfsz,istat,loedge,hiedge,ampth,iendpt
    byte nmbr(6)
    data ibfsz/9216/,nmbr/6*0/
    common /smp1/snm,loedge,hiedge,ampth
    smp = ismp
    istat = 0
    irtsmp = 0
    iendpt = ismp + npts*deld
    if (iendpt .gt. 9216) iendpt = iendpt - 9216
```

... Check curwrt buffer edges to see that data being analyzed does not get
... written over. If data is overrun by sampler a status = 1 is sent,
... otherwise status = 0

```
    if (deld .lt. 0) go to 56       !if neg.directed peak search goto 57 if (ismp .gt. hiedge) go to 52  !if high edge of written buffer is
    if (ismp .lt. loedge) go to 52  !greater than ismp or low edge of
    istat = 1                       !written buffer is .ge. than ismp
    call cvtdec(ismp,nmbr)          !then data is overrun by sampler
    call print('data overrun at ismp:')
    call print(nmbr)
    return 52 if (iendpt .lt. loedge) go to 60  !if trailing edge of curwrt is
    if (iendpt .gt. hiedge) go to 60  !.le.ismp,wait for next buffer
    go to 52
```

```
56  if (lendpt .gt. hiedge) go to 58
    if (lendpt .lt. loedge) go to 58
    intnt = 1
    call cvtdec(lsmp,nmbrx)                    !then data is overrun by sampler
    call print('lendpt at overrun is:')
    call print(nmbrx)
    return 58  if (lsmp .lt. loedge) go to 60
    if (lsmp .gt. hiedge) go to 60
    go to 58

... Now at peak detecting logic:

60  if (ampth .lt. 0) goto 100                 !goto negdirected qrs logic if neg qrs
    do 62 i = 1,npts                           !Check for smp above amp threshold
    j = i
    if (sam(smp) .ge. ampth) go to 63
    smp = smp + deld
    if (smp .gt. tbfsz) smp = smp-tbfsz        !check for positive wraparound
    if (smp .le. 0) smp = smp + tbfsz          !check for negative wraparound
62  continue
    go to 280
63  lsvmax = sam(smp)
    do 75 i = j,npts                           !Check if position is on downslope...
    k = i
    smp = smp + deld if (smp .gt. tbfsz) smp = smp-tbfsz        !check for positive wraparound
    if (smp .le. 0) smp = smp + tbfsz          !check for negative wraparound
    if (sam(smp) .gt. lsvmax) go to 65         !look for downslope
    lsvmax = sam(smp)
75  continue
    go to 280
65  do 76 i = k,npts                           !Now that we're on an upslope next downslope
    if (sam(smp) .lt. lsvmax) goto 275         !look for +/- trans.
    lsvmax = sam(smp)
    smp = smp + deld
    if (smp .gt. tbfsz) smp = smp-tbfsz        !check for positive wraparound
    if (smp .le. 0) smp = smp + tbfsz          !check for negative wraparound
76  continue
    go to 280
100 do 162 i = 1,npts                          !Check for sample value below threshold
    j = i
    if (sam(smp) .le. ampth) go to 163
    smp = smp + deld
    if (smp .gt. tbfsz) smp = smp-tbfsz        !check for positive wraparound
    if (smp .le. 0) smp = smp + tbfsz          !check for negative wraparound
162 continue
    go to 280
163 lsvmax = sam(smp)
    do 175 i = j,npts
    k = i
    smp = smp + deld
    if (smp .gt. tbfsz) smp = smp-tbfsz        !positive wraparound
    if (smp .le. 0) smp = smp + tbfsz          !negative wraparound
    if (sam(smp) .lt. lsvmax) goto 165         !look for up slope
    lsvmax = sam(smp)
175 continue
    go to 280
165 do 176 i = k,npts
    if (sam(smp) .gt. lsvmax) go to 275        !look for -/+ transition
    lsvmax = sam(smp)
    smp = smp + deld
    if (smp .gt. tbfsz) smp = smp-tbfsz        !positive wraparound
    if (smp .le. 0) smp = smp + tbfsz          !negative wraparound
176 continue
    go to 280
275 lrtsmp = smp - deld
280 return
    end
```

Subroutine I24COR takes two arrays(one 1*2 and the second 1*4) and computes their correlation coefficient over NPTS sample points at intervals of DELD using SYSLIB 1*4 mnth routines. The return argument CORR is a r*4 variable.
The first argument passed is the index to the sample array SAM.
The second argument is the array to be correlated against SAM.

```
    subroutine i24cor(index,array,npts,deld,corr,istat)
    integer sam(9216),i,j,index,npts,deld,ibeats,istat,loedge,
   .        hiedge,iendpt,nmpth,init(10)
    integer*4 array(npts),sum0,sum1,sum2,tmp1,tmp2,tmp3,
   .        ibeat,temp1,temp2
    real corr,num,den1,den2
    byte nmbr(6)
    equivalence (sum0,init(1)),(sum1,init(3)),(sum2,init(5)),
   .        (temp1,init(7)),(temp2,init(9))
    common /smpl/sam,loedge,hiedge,ampth
    common /chn/ichn,ibeats
    istat = 0
    iendpt = index + npts*deld
    if (iendpt .gt. 9216) iendpt = iendpt-9216

.. Check for data overrun by sampler or sampler overrun by program logic:

if (index .gt. hiedge) go to 50
    if (index .lt. loedge) go to 50
    call cvtdec(index,nmbr)
    call print('data overrun at index:')
    call print(nmbr)                              !error data overrun
    istat=1
    return 50  if (iendpt .lt. loedge) go to 60
    if (iendpt .gt. hiedge) go to 60
    go to 50

60  call jicvt(ibeats,ibeat)

.. Initialize variables
    do 62 i = 1,10
        init(i) = 0
62  continue do 100 i = 1,npts
        if (index .gt. 9216) index = index - 9216   !Check for pos.wraprnd
        call jicvt(sam(index),temp1)
        j = jdiv(array(i),ibeat,temp2)
        j = jmul(temp1,temp2,tmp1)
        j = jadd(tmp1,sum0,sum0)
        j = jmul(temp1,temp1,tmp2)
        j = jadd(tmp2,sum1,sum1)
        j = jmul(temp2,temp2,tmp3)
        j = jadd(tmp3,sum2,sum2)
        index = index + deld
100 continue
    num = ajflt(sum0)
    den1 = ajflt(sum1)
    den2 = ajflt(sum2)
    corr = num/sqrt(den1*den2)
    return
    end
```

Subroutine I22COR performs the same function as I24COR but on two sections of sam indexed by INDEX1 & INDEX2 using 1*4 mnth.

```
    subroutine i22cor(index1,index2,npts,deld,corr,istat)
    integer sam(9216),i,j,index1,index2,npts,deld,ibeats,
   .        istat,loedge,hiedge,nmpth,init(10)
    integer*4 sum0,sum1,sum2,temp1,temp2,tmp1,tmp2,tmp3
    real corr,num,den1,den2
    equivalence (init(1),sum0),(init(3),sum1),(init(5),sum2),
   .        (init(7),temp1),(init(9),temp2)
    common /smpl/sam,loedge,hiedge,ampth
    common /chn/ichn,ibeats
    istat = 0

... Initialize variables do 50 i = 1,10
        init(i) = 0
```

```
50    continue
      do 100 I = 1,npts
            if (index1 .gt. 9216) index1 = index1-9216    !Check for pos.wrprnd
            if (index2 .gt. 9216) index2 = index2-9216
            call jicvt(sam(index1),temp1)
            call jicvt(sam(index2),temp2)
            j = jmul(temp1,temp2,tmp1)
            j = jadd(tmp1,sum0,sum0)
            j = jmul(temp1,temp1,tmp2)
            j = jadd(tmp2,sum1,sum1)
            j = jmul(temp2,temp2,tmp3)
            j = jadd(tmp3,sum2,sum2)
            index1 = index1 + deld
            index2 = index2 + deld
100   continue
      num = ajflt(sum0)
      den1 = ajflt(sum1)
      den2 = ajflt(sum2)
      corr = num/sqrt(den1*den2)
      return
      end
```

PROGRAM NO. 2

```
PDP-11 FORTRAN-77 V4.0-3      15:52:38    5-Dec-83
ECGFFT.FOR;1              /F77/TR:BLOCKS/WR c  and FFTing.  NPLOT is the number of plot sets to be done.
0006           integer nsamp(10)
0007           integer nixsmp(10),niysmp(10)
0008           integer nplot
         c
         c  These vars. are used to calculate the composite beat.
0009           real cwave(1024),temp1,temp2,temp3
         c
         c  FFT_ hold the windowed data to be output to disk.
0010           real fft0(514),fft1(514),fft2(514),fftc(514)
         c
0011           byte query(80)
0012           byte cr
0013           byte nmbrx(7)
0014           byte input(6)
0015           byte infile(10)
0016           byte outfil(11)
0017           byte output(6)
         c
0018           equivalence (ichn,iobuff(1)),(jchn,iobuff(2)),(kchn,iobuff(3)),
              .(iwave,iobuff(4)),(jwave,iobuff(1028)),(kwave,iobuff(2052))
0019           equivalence (input,infile),(output,outfil)
         c
0020           common /zoom/gainx,gainy
         c
0021           data idnam/3RDY /
0022           data dblk/3RDY1,0,0,0/
0023           data nmbrx/7*0/
0024           data nplot/0/
0025           data nsamp/10*0/
0026           data infile/6*40,'D','A','T',0/
0027           data outfil/6*40,'.','F','F','T',0/
         c
         c...  Initialize:
         c
0028           gainx = 0
0029           gainy = -4
         c
0030           call print('Welcome to ECGFFT version 1.0')
         c
         c...  set up I/O channel:
         c
0031           iochan = igetc()
0032           if (iochan .lt. 0) stop 'No channel available'
0033      25   call print('Enter name of input file: (6chars)')
0034           read(5,27) input
```

```
0035           27 format(6a)
0036           72 call print('Enter the number of plots to run: (0-10)')
0037              read(5,74) nplot
0038           74 format(I6)
0039              if (nplot .eq. 0) go to 69
0040              call print('Enter name of output file: (6chars)')
0041              read(5,27) output
              c
              c... Establish input channel:
              c
```

PDP-11 FORTRAN-77 V4.0-3      15:52:38    3-Dec-83
ECGFFT.FOR;1                  /F77/TR:BLOCKS/WR

```
              c and FFTing. NPLOT is the number of plot sets to be done.
                    integer nsamp(10)
0006                integer nlxsmp(10),nlysmp(10)
0007                integer nplot
0008
              c
              c These vars. are used to calculate the composite beat..
0009                real cwave(1024),temp1,temp2,temp3
              c
              c FFT_ hold the windowed data to be output to disk.
0010                real fft0(514),fft1(514),fft2(514),fftc(514)
              c
0011                byte query(80)
0012                byte cr
0013                byte nmbrx(7)
0014                byte input(6)
0015                byte infile(10)
0016                byte outfil(11)
0017                byte output(6)
              c
                    equivalence (ichn,iobuff(1)),(jchn,iobuff(2)),(kchn,iobuff(3)),
0018               .(lchn,iobuff(4)),(jwave,iobuff(1028)),(kwave,iobuff(2052))
                    equivalence (input,infile),(output,outfil)
0019          c
0020                common /zoom/gainx,gainy
              c
0021                data idnam/3RDY /
0022                data dblk/3RDY1,0,0,0/
0023                data nmbrx/7*0/
0024                data nplot/0/
0025                data nsamp/10*0/
0026                data infile/6*40,'D','A','T',0/
0027                data outfil/6*40,'.','F','F','T',0/
              c
              c... Initialize:
              c
0028                gainx = 0
0029                gainy = -4
              c
0030                call print('Welcome to ECGFFT version 1.0')
              c
              c... set up I/O channel:
              c
0031                iochan = igetc()
0032                if (iochan .lt. 0) stop 'No channel available'
0033           25 call print('Enter name of input file: (6chars)')
0034                read(5,27) input
0035           27 format(6a)
0036           72 call print('Enter the number of plots to run: (0-10)')
0037                read(5,74) nplot
0038           74 format(I6)
0039                if (nplot .eq. 0) go to 69
0040                call print('Enter name of output file: (6chars)')
0041                read(5,27) output
              c
              c... Establish input channel:
```

PDP-11 FORTRAN-77 V4.0-3      15:52:38    3-Dec-83
ECGFFT.FOR;1                  /F77/TR:BLOCKS/WR

```
0042           69 i = irad50(9,infile,dblk(2))
0043                if (i .ne. 9) goto 25
0044                if (lfetch(idnam) .ne. 0) stop 'fatal error fetching handler'
0045                if (lookup(iochan,dblk) .lt. 0) stop 'lookup error'
              c
              c... Read in ichn,jchn,kchn & data:
```

```
0046            icode = ircudw(3075,iobuff,0,iochan)
0047            call cvtdec(icode,nmbrx)
0048            call print(nmbrx)
                if (icode .lt. 0) stop 'Error inputting data'
0049            if (iclose(iochan) .lt. 0) stop 'Error closing file'
0050            if (ifreec(iochan) .lt. 0) stop 'Channel not allocated'
0051
        c
        c...   Compute composite channel:
        c
0052            do 75 i = 1,1024
0053               temp1 = float(iwave(i))
0054               temp2 = float(jwave(i))
0055               temp3 = float(kwave(i))
0056               cwave(i) = sqrt(temp1*temp1 + temp2*temp2 + temp3*temp3)
0057               fwave(i) = int(cwave(i))
0058        75  continue
0059            go to (81,82,83),ichn+1
        c
        c...   If ichn = 0, then reset channels as follows
        c
0060        81  ichn = 2
0061            jchn = 0
0062            kchn = 1
0063            go to 84
        c...   If ichn = 1
0064        82  ichn = 0
0065            jchn = 1
0066            kchn = 2
0067            go to 84
        c...   If ichn = 2 then
0068        83  ichn = 1
0069            jchn = 2
0070            kchn = 0
0071        84  continue
        c
        c...   Enter Selenar mode and plot out data
        c
0072            call clrtrm()
0073            call setsel()
0074            call clrscn()
0075            call stgrph()
0076            call stzoom(gainx,gainy)
0077            call swvplt(iwave,1024,(4-ichn)*50,1)
0078            call swvplt(jwave,1024,(4-jchn)*50,1)
0079            call swvplt(kwave,1024,(4-kchn)*50,1)
0080            call swvplt(fwave,1024,25,1)
0081            call sreset()
0082            call settrm()
0083            if (nplot .eq. 0) go to 250
```

PDP-11 FORTRAN-77 V4.0-3          15:52:38        5-Dec-83
ECGFFT.FOR;1                /F77/TR:BLOCKS/WR

```
0084            do 100 k = 1,nplot
0085               call print('Position cursor at 1st point:
               .(press <cr> to cont.)')
0086               call setsel()
0087               call oncrsr()
0088        80     cr = ittinr()
0089               if (cr .ne. 13) go to 80
0090               cr = ittinr()
0091               call getcrs(ix1,iy)
0092               call offcrs()
0093               call stgrph()
0094               call sline(ix1,1000,ix1,50)
0095               call sreset()
0096               call settrm()
0097               call clrtrm()
0098               call print('Position cursor at 2nd point:
               .(press <cr> to cont.)')
0099               call setsel()
0100               call oncrsr()
0101        90     cr = ittinr()
0102               if (cr .ne. 13) go to 90
0103               cr = ittinr()
0104               call getcrs(ix2,iy)
0105               call offcrs()
```

```
0106                         call sigrph()
0107                         call sline(1x2,1000,1x2,50)
0108                         call sreset()
0109                         call settrm()
0110                         call clrtrm()
0111                         NIXSMP(K) = IX1
0112                         NIYSMP(K) = IX2
0113                         nsamp(k) = 1x2-1x1
0114       100           continue
      c
      c... Open channel and output number of plots:
      c
0115           OPEN(UNIT=1,NAME=outfil,TYPE='NEW',FORM='FORMATTED')
0116           write(1,105)nplot
0117       105 format(16)
      c
      c... Load windowed data into fft arrays:
      c
0118           do 160 l = 1,nplot
0119              do 110 i = nixsmp(l),niysmp(l)
0120                 iitmp = i-nixsmp(l)+1
0121                 fft0(iitmp) = float(iobuff(1+4+ichn*1024))
                                    *wndw(iitmp,nsamp(l))
0122                 fft1(iitmp) = float(iobuff(1+4+jchn*1024))
                                    *wndw(iitmp,nsamp(l))
0123                 fft2(iitmp) = float(iobuff(1+4+kchn*1024))
                                    *wndw(iitmp,nsamp(l))
0124                 fftc(iitmp) = cwave(i)*wndw(iitmp,nsamp(l))
0125       110     continue
      c
      c... Zero out (decimate) the remainder of the FFT arrays:
```

```
c With the actual computation and plotting of the FFT's being done on another
c computer (the Inter-data or perkin-elmer) and since the data transfer from
c the LSI-11 to the Inter-Data is so slow, only the beginning of the array
c with the windowed data is sent out so the decimation here is not really
c neccessary.
126              do 120 i = nsamp(l)+1,514
127                 fft0(i) = 0.
128                 fft1(i) = 0.
129                 fft2(i) = 0.
130                 fftc(i) = 0.
131      120     continue
      c
      c... Output the windowed data to disk, the number of points and the arrays:
      c
132              write(1,125)nsamp(l)
133      125     format(16)
      c
      c... Output arrays:
      c
134      130     format(e13.6)
135              do 140 i = 1,nsamp(l)
136                 write(1,130)fft0(i)
137      140     continue
138              do 145 i = 1,nsamp(l)
139                 write(1,130)fft1(i)
140      145     continue
141              do 150 i = 1,nsamp(l)
142                 write(1,130)fft2(i)
143      150     continue
144              do 155 i = 1,nsamp(l)
145                 write(1,130)fftc(i)
146      155     continue
147      160 continue
      c
      c... Close Channel:
      c
148           CLOSE(UNIT=1)
      c
149      250 call print('Bye bye')
150           stop
151           end
```

PROGRAM NO. 3

PLOTBS

```
C.     READ FROM DISC AND COMPUTE FFT. AND PLOT DATA FOR DA
C.     MODIFY TO REMOVE ZERO OFF-SET
C.     JOANNE HART HAN    JAN  1983
C.
       IMPLICIT INTEGER*2 (I-N)
       DIMENSION X(512),Y(1024),Z(5),ZY(5)
       COMPLEX C(512)
       EQUIVALENCE (C(1),Y(1))
C.
       PNT=FLOAT(Z'5555')
C.
       READ (3) ISET
       ISET=1
  5    CONTINUE
       IPLOT=1
       X0=-0.1
       Y0=7.2
       XMIN=0.
       XMAX=520.
       YMIN=-40.
       YMAX=120.
       XL=6.5
       YL=2.
       XE=X0+XL
       NOP=257
       XINC=40.
       XT=.5
       YINC=40.
       YT=0.5
  10   CONTINUE
       YE=Y0+YL
       J=1
       DO 20 I=1,8
       K=J+63
       READ (3) (X(II),II=J,K)
  20   J=J+64
 1001  FORMAT (10F12.2)
       DO 40 I=1,512
       C(I)=CMPLX(X(I),0.0)
  40   CONTINUE
       M=9
       CALL FFT(C,M)
C.     COMPUTE Y = 20*LOG10(F), X(I)=K*1000/512
C.     CALCULATE AREA FROM 0 TO DECREASE OF 60 DB
C.
 1002  FORMAT (10E12.4)
       J=1
       YMAX=0.
       DO 100 I=1,NOP
       X(I)=(I-1)*1000./512.
       TEMP=SQRT(Y(J)*Y(J)+Y(J+1)*Y(J+1))
       IF (TEMP.EQ.0.) GO TO 80
       Y(I)=20.*ALOG10(TEMP)
       GO TO 90
  80   Y(I)=YMIN
  90   IF (YMAX.GT.Y(I)) GO TO 100
       YMAX=Y(I)
 100   J=J+2
 1003  FORMAT (5(F10.1,F10.2))
```

```
C.
C.      AREA
C.
        YJ=Y(1)-60.
        A=Y(1)
          DO 110 I=2,500
          IF(Y(I).LT.YJ)GO TO 120
110       A=A+Y(I)
120       A=A*1000./512
C.      FIND VALUE AT 40HZ
        R=(40.-X(21))/(X(22)-X(21))
        B=Y(21)+R*(Y(22)-Y(21))
        B=Y(1)-B
        CALL MODE (4,0.07,0.05,0.)
        ZX(1)=X0
        ZX(2)=XE
        ZY(1)=Y0
        ZY(2)=Y0
        CALL DRAW (ZX,ZY,2,1)
        XX=X0
        FN=0.
        ZY(1)=Y0-0.04
        ZY(2)=Y0
        YA=Y0-.15
        DO 220 I=1,20
        IF (XX.GT.XE) GO TO 240
        ZX(1)=XX
        ZX(2)=XX
        CALL DRAW (ZX,ZY,2,1)
        YA=XX-0.11
        IF (FN.LT.10.) YA=XX-.05
        CALL NOTE (XX,YA,FN,1000)
        FN=FN+XINC
        XX=XX+XT
220     CONTINUE
240     CONTINUE
C.
C.      DRAW DASHED LINES FOR X-GRID
C.
        XX=X0
        CALL MODE (10,PAT,3909,.1.)
        ZY(1)=Y0
        ZY(2)=YE
        DO 250 I=1,20
        XX=XX+XT
        IF (XX.GT.XE) GO TO 260
        ZX(1)=XX
        ZX(2)=XX
        CALL DRAW (ZX,ZY,2,1)
250     CONTINUE
260     CONTINUE
C.
C.      DRAW DASHED GRID FOR Y AXIS
C.
        YY=Y0
        ZX(1)=X0
        ZX(2)=XE
        DO 280 I=1,20
        YY=YY+YT
        IF (YY.GT.YE) GO TO 300
        ZY(1)=YY
        ZY(2)=YY
280     CALL DRAW (ZX,ZY,2,1)
C.
C RESET LINE TO SOLID
```

```
C
300   CONTINUE
      CALL NOTE (10.,-1.,9999.,1.)
C
C     DRAW Y AXIS AND LABEL
C
      ZX(1)=X0
      ZX(2)=X0
      ZY(1)=Y0
      ZY(2)=YE
      CALL DRAW (ZX,ZY,2,1)
      ZX(1)=X0-0.05
      ZX(2)=X0
      YY=Y0
      YH=YMIN
      DO 320 I=1,20
      IF (YY.GT.YE) GO TO 350
      ZY(1)=YY
      ZY(2)=YY
      CALL DRAW (ZX,ZY,2,1)
      YJ=ZY(1)-0.05
      XJ=X0-.3
      IF (ABS(YH) .GE.100.) XJ=X0-.36
      IF (YH.EQ.0.) XJ=X0-.15
      CALL NOTE (XJ,YJ,YH,1000)
      YH=YH+YINC
320   YY=YY+YT
350   CALL MODE (4.0.1.0.067.0.)
      YJ=Y0+1.8
      CALL NOTE (5.,YJ,'AREA=',5)
      CALL NOTE (5.6,YJ,A,1000)
      YJ=YJ-.2
      CALL NOTE (5.0,YJ,'F(40HZ)=',8)
      CALL NOTE (6.0,YJ,B,1000)
      XS=XT/XINC
      YS=YT/YINC
      DO 400 I=1,NOP
      X(I)=X(I)*XS+X0
      Y(I)=(Y(I)-YMIN)*YS+Y0
400   CONTINUE
      CALL DRAW (X,Y,NOP,1)
      XJ=X0-.38
      YJ=Y0+.5
      CALL MODE (4.0.1.0.067.90.)
      CALL NOTE (XJ,YJ,'FFT-MAG (DB)',12)
      CALL MODE (4.0.1.0.067.0.)
      XJ=X0+XL/2.-.5
      YJ=Y0-.3
      CALL NOTE (XJ,YJ,'FREQ (HZ)',9)
      IF (IPLOT.EQ.4) GO TO 500
      IPLOT=IPLOT+1
      Y0=Y0-2.4
      GO TO 10
500   CALL DRAW (0.,0.,1,9000)
      IF (ISET.EQ.NSET) GO TO 600
      ISET=ISET+1
      GO TO 5
600   CONTINUE
      CALL DRAW (0.,0.,0,9999)
      STOP
      END
```

```
C     READ FROM DISC AND COMPUTE FFT. AND PLOT DATA FOR DA
C     JOHNIE HAPKHAM    JAN 1983
C     MODIFY FOR POWER SPECTRUM   NOV 1983
C     SCALE INPUT DATA TO 1.0
C     MODIFY FOR 2 PLOTS ON SINGLE SCALE
C
      IMPLICIT INTEGER*2 (I-N)
      DIMENSION X(512),Y(1024),ZX(5),ZY(5),Z(512)
      DIMENSION IPEAK(10)
      COMPLEX C(512)
      EQUIVALENCE (C(1),Y(1))
      EQUIVALENCE (Y(513),Z(1))
C
      PAT=FLOAT(X'5555')
C
      READ (3) NSET
      ISET=1
5     CONTINUE
      IPLOT=1
      X0=0.
      Y0=7.2
      XMIN=0.
      XMAX=120.
      YMIN=0.
      XL=6.
      YL=2.
      XE=X0+XL
      NOP=61
      XINC=10.
      XT=.5
      YT=0.5
10    CONTINUE
      YE=Y0+YL
      J=1
      DO 20 I=1,8
      K=J+63
      READ (3) (X(M),M=J,K)
20    J=J+64
1001  FORMAT (10E12.2)
      S=0.
      YM=0.
      DO 30 I=1,512
      IF (ABS(X(I)).LE.YM) GO TO 30
      YM=ABS(X(I))
30    S=S+X(I)
      DO 35 I=1,512
      K=513-I
      IF (X(K).NE.0.) GO TO 37
35    CONTINUE
37    CONTINUE

S=S/K
1009  FORMAT (' MEAN =',F10.4)
      DO 40 I=1,512
      X(I)=X(I)/YM
      C(I)=CMPLX(X(I),0.0)
40    CONTINUE
      WRITE (6,1031) (X(I),I=1,K)
1031  FORMAT ('1DATA AFTER SCALING'/(10F10.4))
      WRITE (6,1009) S
      M=9
      CALL FFT(C,M)
C     COMPUTE POWER SPECTRUM
C
1002  FORMAT (10E12.4)
      J=1
      FMAX=0.
```

```
       DO 100 I=1,257
       X(I)=(I-1)*1000./512.
       Y(I)=(Y(J)*Y(J)+Y(J+1)*Y(J+1))-
       IF (FMAX.GT.Y(I)) GO TO 100
90     FMAX=Y(I)
       JK=I
100    J=J+2
1003   FORMAT (5(F10.1,F10.2))
       WRITE (6,1007) FMAX,(Y(I),I=1,150)
1007   FORMAT ('0AUTO-CORRELATION ',F10.3/(10E12.4))
       WRITE (6,1040) IPLOT,ISET
1040   FORMAT ('1 PLOT ',I3,'   OF SET ',I3/)
C.     AREA FROM  0-20 HZ & 20-50 HZ
       AR=0.
       DO 700 I=1,11
700    AR=AR+Y(I)
       AR=AR*X(2)
       ARB=0.
       DO 720 I=12,27
720    ARB=ARB+Y(I)
       ARB=ARB*X(2)
       R=ARB/AR
       WRITE (6,1041) AR,ARB,R
1041   FORMAT ('0  AREA FROM  0-20 HZ  = ',E14.5,/
      1'0  AREA FROM 20-50 HZ  = ',E14.5,5X,'RATIO =',E14.5)
       WRITE (6,1042) Y(JK),X(JK)
1042   FORMAT ('0 PEAK = ', F10.2, ' AT ',F8.2,' HZ'/)
       R=AR/FMAX
       WRITE(6,1043)R
1043   FORMAT ('0 AREA 0-20 HZ/PEAK =',F14.4)
C.  FIND PEAKS  FROM 20-50 HZ ( POINTS NO 8-27)
       NPK=0
       IP=0
       ID=1
       SAVE =Y(7)
C.
       DO 880 I=8,27
       SUM=Y(I)
       DIF =SUM-SAVE
       IF (DIF) 810,870,840
810    CONTINUE
       ID=ID +1
       IF (ID.EQ.1) GO TO 820
       IP=0
       GO TO 870
820    IF (IP.LT.2) GO TO 870
       IF (NPK.EQ.10) GO TO 890
       NPK=NPK+1
       IPEAK(NPK)=I-1
       IP=0
       GO TO 870
840    IP=IP+1
       ID=0
870    SAVE =SUM
880    CONTINUE
       GO TO 895
890    WRITE (6,1047)
1047   FORMAT (' MORE THAN 10 PEAKS FOUND--ONLY 1ST 10 ACCEPTED')
895    WRITE (6,1046)NPK
1046   FORMAT ('0',I4,' PEAKS FOUND FROM FREQ 20-50 HZ'//6X,
      1'FREQ',11X,'PEAK',11X,'RATIO'//)
       IF (NPK.EQ.0) GO TO 898
       DO 897 I=1,NPK
       J=IPEAK(I)
       R=Y(J)/FMAX
897    WRITE (6,1048)X(J),Y(J),R
1048   FORMAT (F10.2,E15.4,F15.4)
898    CONTINUE
       DV=0.1
120    K=FMAX/DV
```

```
            IF (K.EQ.0) GO TO 140
            DV=DV*10.
            GO TO 120
  140       CONTINUE
            K=(FMAX*10/DV)+1
            YMAX=(K*DV)/10.
            YINC=YMAX/4.
C     DRAW X AXIS
            CALL MODE (4,0,07,0.05,0.)
            ZX(1)=X0
            ZX(2)=XE
            ZY(1)=Y0
            ZY(2)=Y0
            CALL DRAW (ZX,ZY,2,1)
            XX=X0
            FN=0.
            ZY(1)=Y0-0.04
            ZY(2)=Y0
            YA=Y0-.15
            DO 220 I=1,20
            IF (XX.GT.XE) GO TO 240
            ZX(1)=XX
            ZX(2)=XX
            CALL DRAW (ZX,ZY,2,1)
            XA=XX-0.11
            IF (FN.LT.10.) XA=XX-.03
            CALL NOTE (XA,YA,FN,1000)
            FN=FN+XINC
            XX=XX+XT
  220       CONTINUE
  240       CONTINUE
C     DRAW DASHED LINES FOR X-GRID
            XX=X0
            CALL MODE (10,PAT,9999.,1.)
            ZY(1)=Y0
            ZY(2)=YE
            DO 250 I=1,20
            IF (XX.GT.XE) GO TO 260
            ZX(1)=XX
            ZX(2)=XX
            CALL DRAW (ZX,ZY,2,1)
            XX=XX+XT
  250       CONTINUE
  260       CONTINUE
C     DRAW DASHED GRID FOR Y AXIS
            YY=Y0
            ZX(1)=X0
            ZX(2)=XE
            DO 280 I=1,20
            YY=YY+YT
            IF (YY.GT.YE) GO TO 300
            ZY(1)=YY
            ZY(2)=YY
  280       CALL DRAW (ZX,ZY,2,1)
C RESET LINE TO SOLID
  300       CONTINUE
            CALL MODE (10,-1.,9999.,1.)
C     DRAW Y AXIS AND LABEL
      LN=1000
      IF (FMAX.LT.1.0) LN=1002
      IF (FMAX.LT.10.) LN=1001
      ZX(1)=X0-0.05
      ZX(2)=X0
      YY=Y0
      YN=YMIN
      DO 320 I=1,20
      IF (YY.GT.YE) GO TO 350
      ZY(1)=YY
      ZY(2)=YY
```

```
              CALL DPAW (ZX,ZY,2,1)
                 YJ=ZY(1)-0.05
                 XJ=X0-.3
          IF (ABS(YN) .GE.100.) XJ=X0-.4
          IF (YN.EQ.0.) XJ=X0-.15
              CALL NOTE (XJ,YJ,YN,LN)
                 YN=YN+YINC
320              YY=YY+YT
350          CONTINUE
          ZX(1)=XE
          ZX(2)=XE
          ZY(1)=Y0
          ZY(2)=YE
          LN=1001
          CALL DPAW (ZX,ZY,2,1)
          YINCB=YINC/500.
          YN=YMIN
          ZX(2)=XE+0.05
          YY=Y0
          DO 360 I=1,20
           IF (YY.GT.YE) GO TO 370
           ZY(1)=YY
           ZY(2)=YY
           CALL DRAW (ZX,ZY,2,1)
              YJ=ZY(1)-0.05
              XJ=XE+0.1
              CALL NOTE (XJ,YJ,YN,LN)
                 YN=YN+YINCB
                 YY=YY+YT
360          CONTINUE
370          CONTINUE
          CALL MODE (4,0,1,0.067,0.)
              YJ=Y0+1.8
              XS=XT/XINC
              YS=YT/YINC
              DO 400 I=1,NOP

X(I)=X(I)*XS+X0
                 Z(I)=(Y(I)-YMIN)*YS+Y0
400              CONTINUE
          CALL MODE (10,PAT,9999.,1.)
              CALL DRAW (X,Z,NOP,1)
          CALL MODE (10,-1,.9999.,1.)
              YS=YT/YINCB
              DO 420 I=1,NOP
              Y(I)=(Y(I)-YMIN)*YS +Y0
              IF (Y(I).GT.YE) Y(I)=YE
420          CONTINUE
              CALL DPAW ( X,Y,NOP,1)
                 XJ=X0-.53
                 YJ=Y0+.5
              CALL MODE (4,0,1,0.067,90.)
              CALL NOTE (XJ,YJ,'AUTO-CORR   ',12)
              CALL MODE (4,0,1,0.067,0.)
          XJ=X0+XL/2.-.5
          YJ=Y0-.3
          CALL NOTE (XJ,YJ,'FREQ (HZ)',9)
              IF (IPLOT.EQ.4) GO TO 500
          IPLOT=IPLOT+1
              Y0=Y0-2.4
              GO TO 10
500          CALL DRAW (0.,0.,1,9000)
          IF (ISET.EQ.NSET) GO TO 600
          ISET=ISET+1
          GO TO 5
600       CONTINUE
              CALL DRAW (0.,0.,0.9999)
              STOP
              END
```

What is claimed is:

1. A method for analyzing electrocardiogram (ECG) signals to determine the presence or absence of a predetermined frequency content in a preselected portion of said ECG signals comprising the steps of:
converting analog ECG signals to digital ECG signals;
performing a fast Fourier transform (FFT) on said preselected portion of said digital ECG signals; and
determining a figure of merit (FOM) associated with the frequency content of said at least a preselected portion of said ECG signals from said output of said Fourier transform step, whereby said determination of the presence or absence of said predetermined frequency content can be determined from the vaule of said FOM.

2. The method of claim 1 wherein said method further comprises the step of:
comparing said FOM with a predetermined FOM associated with said predetermined frequency content.

3. The method of claim 2 wherein said step of determining the FOM comprises the steps of:
determining the normalized power level of the FFT output at 40 Hz; and
determining the 60 dB area of the FFT output.

4. The method of claim 3 wherein said method further comprises the step of forming a spectral plot of the FFT output before determining said FOM therefrom.

5. The method of claim 3 wherein said ECG signals comprises X, Y, and Z ECG signals and said step of determining said FOM further comprises:
determining said FOM for each of said X, Y, and Z ECG signals; and
forming the mean of said 40 Hz intercepts and said 60 dB areas from said X, Y, and Z FOM's.

6. The method of claim 3 wherein said preselected portion of said digital ECG signals comprises the terminal portion of said QRS portion and said FOM associated with said predetermined frequency content comprises a 60 dB area greater than 2400 and 40 Hz drop less than 47 dB.

7. The method of claim 3 wherein said preselected portion of said digital ECG signals comprises the ST portion and said FOM associated with said predetermined frequency content comprises a 60 dB area greater than 2500 and 40 Hz drop less than 52 dB.

8. The method of claim 1 wherein said method further comprises the step of:
forming an averaged ECG signal by averaging preselected ones of said digital ECG signals before performing a FFT on at least a portion of said averaged ECG signal.

9. The method of claim 8 wherein said ECG signals comprise X, Y, and Z signals and said method further comprises the steps of:
forming an averaged ECG signal for each of said X, Y, and Z signals;
forming an ECG template;
screening said digital ECG signals through said template to obtain said preselected ones of said digital ECG signals, said step of forming a template further comprising:
selecting model X, Y, and Z signals;
determining the R—R interval between successive QRS portions of a selected one of said model X, Y, and Z signals;
determining the fiducial point of said selected one; and
determining the peak to peak amplitude of each of said model X, Y and Z QRS portions.

10. The method of claim 9 wherein said step of screening said ECG signals comprises the steps of:
choosing candidate X, Y, and Z signals for comparison with said template;
performing a multi-point cross correlation between said selected one of said model X, Y, and Z signals and the corresponding one of said candidate X, Y, and Z signals;
selecting said candidate X, Y, and Z signals as a portion of said preselected ones if said R—R interval of said selected one of said candidate X, Y, and Z signals is within ±20% of said template value; said cross correlation coefficient is greater than or equal to 98%; and at least two out of three of the candidate QRS peak to peak amplitudes are the same as the template values.

11. The method of claim 10 wherein said screening step further comprises selecting said candidate X, Y, and Z signals as a portion of said preselected ones of said digital ECG signals if and only if the X, Y, and Z signals before and after said chosen signal are also acceptable when compared with said template.

12. The method of claim 1 wherein said preselected portion of said ECG signals comprises the terminal 40 milliseconds of the QRS portion.

13. The method of claim 1 wherein said preselected portion of said ECG signals comprises the ST portion of the ECG signal.

14. An apparatus for analyzing electrocardiogram (ECG) signals to determine the presence of a predetermined frequency content in the ECG signal comprising:
A/D means for converting analog ECG signals to digital ECG signals;
FFT means for performing a fast Fourier transform (FFT) on at least a portion of said digital ECG signals; and
means for determining a figure of merit (FOM) for said FFT, said FOM associated with the frequency content of said at least a portion of said digital ECG signals.

15. The apparatus of claim 14 wherein said apparatus further comprises:
comparison means for comparing said FOM with a predetermined FOM associated with said predetermined frequency content.

16. The apparatus of claim 15 wherein said at least a portion of said digital ECG signals comprises the terminal 40 milliseconds of a QRS portion of said ECG signals.

17. The apparatus of claim 15 wherein said at least a portion of said digital ECG signals comprises the ST segment of said ECG signal.

18. The apparatus of claim 16 wherein said predetermined FOM comprises a 60 dB area greater than 2400 and a 40 Hz intercept less than 47 dB.

19. The apparatus of claim 17, wherein said predetermined FOM comprises a 60 dB area greater than 2500 and a 40 Hz intercept less than 52 dB.

20. A method for analyzing electrocardiogram (ECG) signals to determine the presence or absence of a predetermined frequency content in a preselected portion of said ECG signals comprising the steps of:
converting analog ECG signals to digital ECG signals;

forming energy spectra of said preselected portion of said digital ECG signals; and comparing a measure of the energy content of a first preselected portion of said energy spectra with a measure of the energy content of a second preselected portion whereby the presence or absence of a predetermined frequency content is determined.

21. The method of claim 20 wherein the step of forming the energy spectra comprises the steps of:

performing a fast-Fourier transform (FFT) on said ECG preselected portion; and squaring the magnitude of said FFT of said ECG preselected portion.

22. The method of claim 21 wherein said ECG preselected portion comprises a terminal portion of the QRS portion along with the ST portion of said ECG signals.

23. The method of claim 22 wherein the step of comparing an energy measure of the energy content comprises the step of:

comparing the maximum amplitude of each frequency peak in said first preselected portion with the maximum amplitude of the largest peak in said energy spectra.

24. The method of claim 23 wherein said first preselected portion comprises approximately the region from 20 Hz to between 50 and 70 Hz.

25. The method of claim 22 wherein the step of comparing an energy measure of the energy content comprises the step of comparing the area of the energy spectra in said first preselected portion with the area of the energy spectra in said second preselected portion.

26. The method of claim 22 wherein said first preselected portion comprises approximately the region from at least 20 Hz to 50 Hz and said second preselected portion comprises approximately the the region from 0 Hz to 20 Hz.

27. An apparatus for analyzing electrocardiogrm (ECG) signals to determine the presence or absence of a predetermined frequency content in a preselected portion of said ECG signals comprising:

means for converting analog ECG signals to digital ECG signals;

means for forming energy spectra of said preselected portion of said digital ECG signals; and means for comparing a measure of the energy content of a first preselected portion of said energy spectra with a measure of the energy content of a second preselected portion whereby the presence or absence of a predetermined frequency content is determined.

28. The apparatus of claim 27 wherein said means for forming the energy spectra comprises:

means for performing a fast-Fourier transform (FFT) on said ECG preselected portion; and means for squaring the magnitude of said FFT of said ECG preselected portion.

29. The apparatus of claim 28 wherein said ECG preselected portion comprises a terminal portion of the QRS portion along with the ST portion of said ECG signals.

30. The apparatus of claim 29 wherein said means for comparing an energy measure of the energy content comprises:

means for comparing the area of the energy spectra in said first preselected portion with the area of the energy spectra in said second preselected portion.

31. The method of claim 29 wherein said first preselected portion comprises approximately the region from at least 20 Hz to 50 Hz and said second preselected portion comprises approximately the region from 0 Hz to 20 Hz.

32. The apparatus of claim 29 wherein means for comparing an energy measure of the energy content comprises:

means for comparing the maximum amplitude of each frequency peak in said first preselected portion with the maximum amplitude of the largest peak in said energy spectra.

33. The apparatus of claim 32 wherein said first preselected portion comprises approximately the region from 20 Hz to between 50 and 70 Hz.

34. An apparatus for analyzing X, Y, and Z electrocardiogram (ECG) signals to determine the presence of a predetermined frequency content thereof comprising:

A/D means for converting analog X, Y, and Z ECG signals to digital ones;

averaging means for averaging selected ones of each of said X, Y, and Z ECG signals for forming averaged, X, Y, and Z ECG signals;

FFT means for performing a fast Fourier transform (FFT) on at least a portion of each of said averaged X, Y, and Z ECG signals;

means for determining a figure of merit (FOM) from the FFT of each of said averaged X, Y, and Z ECG signals; and comparison means for comparing said FOM with a predetermined FOM associated with said predetermined frequency content.

35. The apparatus of claim 34 wherein said apparatus further comprises:

means for selecting said selected ones of said X, Y, and Z signals for averaging comprising means for comparing said ECG X, Y, and Z signals with a predetermined template of a model ECG signal.

* * * * *